(12) United States Patent
Abe et al.

(10) Patent No.: US 8,642,066 B2
(45) Date of Patent: Feb. 4, 2014

(54) SUSTAINED DRUG DELIVERY SYSTEM

(75) Inventors: Toshiaki Abe, Miyagi (JP); Nobuhiro Nagai, Miyagi (JP); Hirokazu Kaji, Miyagi (JP); Takeaki Kawashima, Miyagi (JP); Matsuhiko Nishizawa, Miyagi (JP); Koji Nishida, Miyagi (JP)

(73) Assignee: Tohoku University, Miyagi (JP)

( * ) Notice: Subject to any disclaimer, the term of this patent is extended or adjusted under 35 U.S.C. 154(b) by 17 days.

(21) Appl. No.: 13/398,051

(22) Filed: Feb. 16, 2012

(65) Prior Publication Data

US 2012/0177717 A1     Jul. 12, 2012

Related U.S. Application Data

(63) Continuation of application No. PCT/JP2010/063793, filed on Aug. 10, 2010.

(30) Foreign Application Priority Data

Aug. 18, 2009 (JP) ................. 2009-189462

(51) Int. Cl.
*A61F 13/00* (2006.01)
*A61P 9/10* (2006.01)

(52) U.S. Cl.
USPC .................... 424/427; 514/20.8; 514/573

(58) Field of Classification Search
None
See application file for complete search history.

(56) References Cited

U.S. PATENT DOCUMENTS

| | | | |
|---|---|---|---|
| 4,327,725 A | | 5/1982 | Cortese et al. |
| 5,614,578 A | | 3/1997 | Dong et al. |
| 5,632,727 A | * | 5/1997 | Tipton et al. ............... 602/47 |
| 5,707,643 A | | 1/1998 | Ogura et al. |
| 5,807,581 A | | 9/1998 | Rosenblatt et al. |
| 6,551,613 B1 | | 4/2003 | Dong et al. |
| 6,706,283 B1 | | 3/2004 | Appel et al. |
| 8,105,629 B2 | | 1/2012 | Yunoki et al. |
| 2003/0064095 A1 | | 4/2003 | Martin et al. |
| 2004/0175410 A1 | | 9/2004 | Ashton et al. |
| 2004/0254197 A1 | | 12/2004 | Tasaka et al. |
| 2006/0127481 A1 | | 6/2006 | Kataoka et al. |

FOREIGN PATENT DOCUMENTS

| | | |
|---|---|---|
| EP | 1 027 888 A2 | 8/2000 |
| JP | 57-93065 A | 6/1982 |
| JP | 4-001124 A | 1/1992 |
| JP | 06-312943 A | 11/1994 |
| JP | 8-34747 A | 2/1996 |
| JP | 10-508023 A | 8/1998 |
| JP | 2000-229846 A | 8/2000 |
| JP | 2002-212062 A | 7/2002 |
| JP | 2002-524151 A | 8/2002 |
| JP | 2002-528043 A | 8/2002 |
| JP | 2002-534139 A | 10/2002 |
| JP | 2003-171315 A | 6/2003 |
| JP | 2005-8614 A | 1/2005 |
| JP | 2005-502426 A | 1/2005 |
| JP | 2006-516621 A | 7/2006 |
| JP | 2007-503265 A | 2/2007 |
| JP | 2007-056014 A | 3/2007 |
| JP | 2007-505932 A | 3/2007 |
| JP | 4064435 B2 | 1/2008 |
| JP | 2008-520547 A | 6/2008 |
| JP | 2008-535847 A | 9/2008 |
| WO | WO 96/13248 A1 | 5/1996 |
| WO | WO 98/53744 A1 | 12/1998 |
| WO | WO 00/13674 A1 | 3/2000 |
| WO | WO 00/40089 A1 | 7/2000 |
| WO | WO 03/024357 A2 | 3/2003 |
| WO | WO 2004/066983 A2 | 8/2004 |
| WO | WO 2005/02706 A1 | 3/2005 |
| WO | WO 2005/020907 A2 | 3/2005 |
| WO | WO 2005/027906 A11 | 3/2005 |
| WO | WO 2006/041942 A2 | 4/2006 |
| WO | WO 2006/110487 A1 | 10/2006 |
| WO | WO 2008/008434 A1 | 1/2008 |

OTHER PUBLICATIONS

International Search Report mailed Sep. 14, 2010 in related International Application PCT/JP2010/063793 (3 pages).
Anders Bill, M.D., "Movement of Albumin and Dextran Through the Sclera," Arch. Ophthalmol., vol. 74, Aug. 1965, pp. 248-252.

* cited by examiner

*Primary Examiner* — Kyle Purdy
(74) *Attorney, Agent, or Firm* — Robert p. Michal; Lucas & Mercanti, L.L.P.

(57) ABSTRACT

Disclosed is a drug delivery system for delivering a drug at a sustained constant rate for a long period, which can be transplanted into an affected part safely and in a simple manner and can deliver a drug to the affected part for a long period. Specifically disclosed is a sustained drug delivery system in which an implant is implanted into a body, wherein the implant is a PEG capsule comprising a box-shaped PEG and a porous PEG sheet.

12 Claims, 31 Drawing Sheets

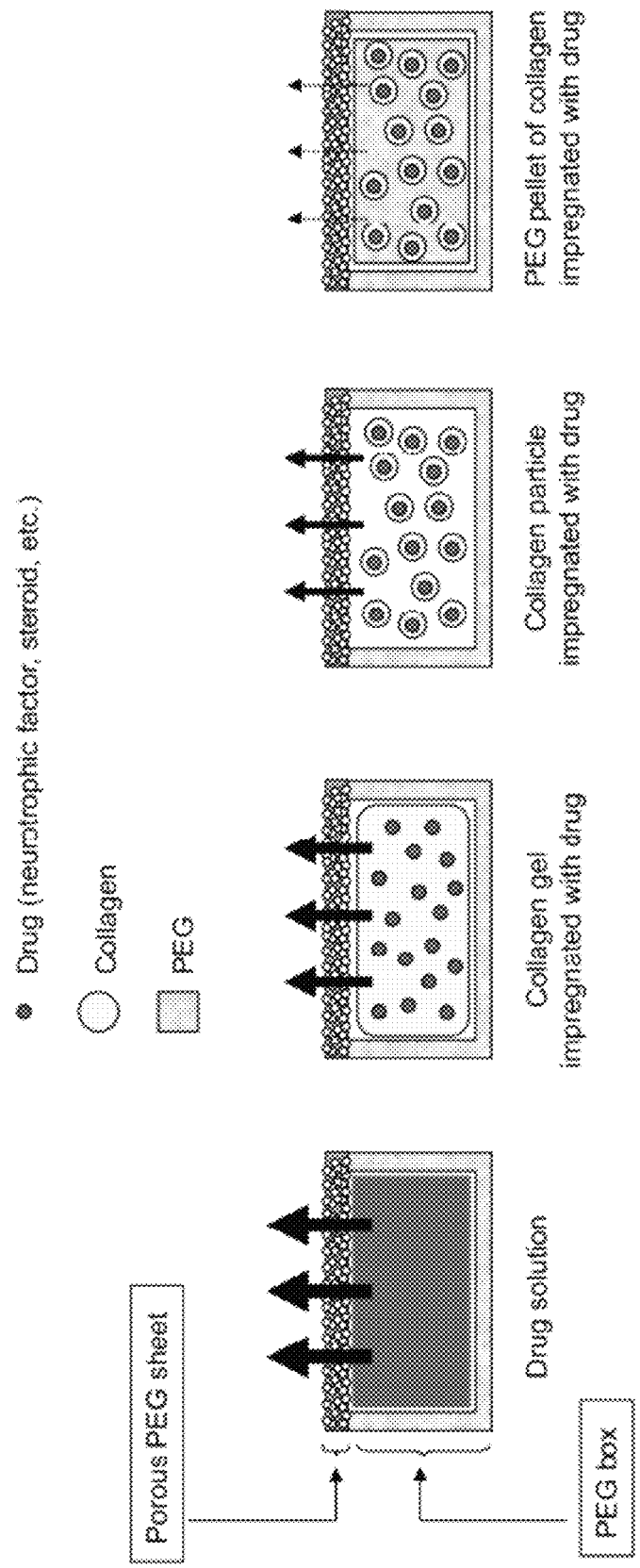

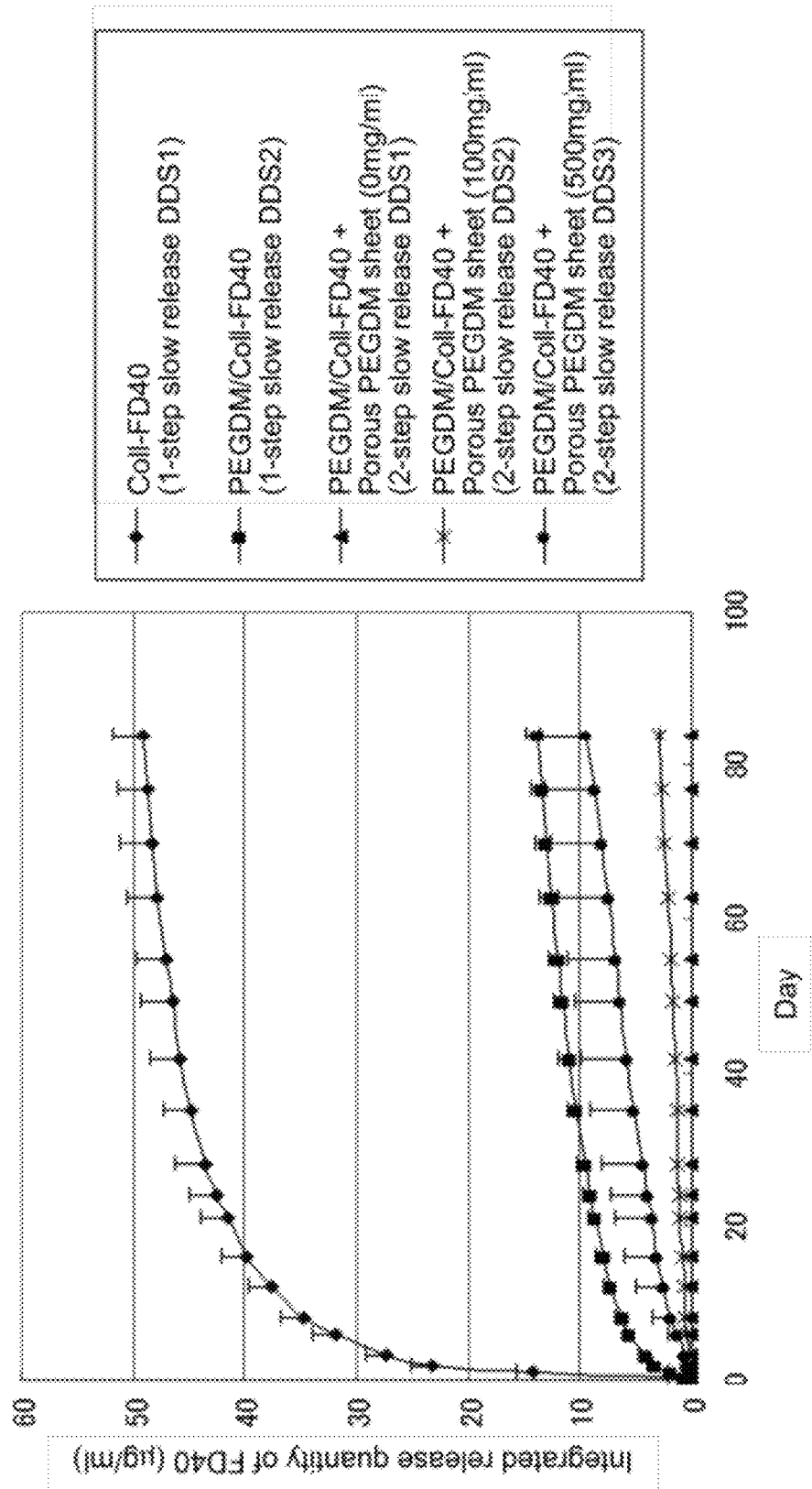

SUSTAINED DRUG DELIVERY SYSTEM

CROSS-REFERENCE TO RELATED APPLICATION

This is a Continuation of PCT International Application PCT/JP2010/063793 filed Aug. 10, 2010, which in turn claims benefit to Japanese Patent Application No. JP 2009-189462 filed Aug. 18, 2009, the entire disclosure of each of which is incorporated herein by reference.

TECHNICAL FIELD

The present invention relates to a drug delivery system (DDS) for delivering a drug at a sustained constant rate for a long period. Specifically, it relates to a DDS and a method for treating the eye of a mammal having a disorder or disease of the eye. More specifically, it relates to an implant and a method for sustained administration of a drug into the eyeball. The use of the implant and method described herein enables the sustained administration of a drug to a desired treatment site, specifically into the eyeball.

BACKGROUND ART

A drug delivery system (DDS) of the concept of "feeding a minimum necessary drug to where the demand is when needed" has been devised as a means for more safely and effectively performing drug chemotherapy. A transdermal DDS for controlling the absorption of an antianginal drug, nitroglycerin, or an antihypertensive drug, clonidine, from the skin and oral DDS using osmotic pressure have been put to practical use as DDS preparations.

Eye disease is generally treated by the instillation administration of a drug. However, some drugs are little transferred to the retina or the vitreous body by this method. It also needs to be considered that the attempt of systemic administration thereof such as intravenous administration may less easily result in transfer to a treatment site as they each approach the effective concentration, due to the blood-aqueous barrier or the blood-retinal barrier, or can cause systemic side effects. A method has recently been attempted for directly injecting a drug into the vitreous body; however, according to this method, the drug is dispersed immediately after injection and metabolized, and the amount of the drug transferred to the target site is several percent or less. Thus, there may be a method which involves injecting a high concentration of the drug; however, it poses a risk of producing side effects on normal intraocular tissue. There is also frequent administration as another method; however, it is not practical in view of the risk of infection and the inconvenience of the procedure.

To solve these problems, a DDS for intraocular therapy has been devised which safely and slowly releases a drug into the eye.

DDS and Implant for Intraocular Therapy

For example, there is a surgical implant, Vitrasert (Bausch & Lomb) for delivering ganciclovir into the eye as a non-degradable DDS. This is a device for surgically implanting a drug reservoir-type implant in the vitreous body. It has a slow-release period of about 3 years. However, in some cases, it requires reoperation to remove the implanted implant, or, when causing side effects, takes long to address them; thus, it is a problem that the risk of infection and the physical burden of a patient are increased. The slowly released drug is dispersed and metabolized in the vitreous body; thus, it is doubtful whether the drug at a curative level reaches a target site.

For example, a "biodegradable scleral plug" is disclosed as a DDS for intraocular therapy (see Patent Literature 1). This is a DDS for which polylactic acid is processed into plug form, punctured into the sclera, and left in place. It is characterized in that a metallic scleral plug used for closing an opening formed by vitreous surgery is prepared using a biodegradable polymer and allowed to include a drug so that the drug is slowly released with the degradation of the polymer and the opening is also closed up due to cure. However, as in the above implant, because the drug is dispersed in the vitreous body, it is doubtful whether the drug at a curative level reaches a target site. In addition, there is a problem of the risk of infection and the physical burden due to the vitreous surgery.

For example, an implant for subjecting a drug-coated core-like polycaprolactone to direct subretinal implantation is disclosed as a DDS for intraocular therapy (see Patent Literature 2). The direct subretinal implantation requires vitreous surgery. Considerable technique is also required for an operator in order to embed the implant in the fragile retinal tissue. The implant is likely to cause infection and nick the retina and highly invasive and therefore not practical.

For example, "a polymer delivery formulation for delivery to an optic portion" is discloses as a DDS for intraocular therapy (see Patent Literature 3). This is a method for intravitreally or subconjunctivally injecting microspheres consisting of lactide/glycolide copolymer, containing a drug using polyethylene glycol as a carrier solvent. However, even the use of such a fluid DDS carrier has a problem that it is easily dispersed to the periphery of a target site, reducing the local effect of the drug.

As described above, these implants of the type of being implanted in the vitreous body are accompanied by the risk of infection and the physical and economic burden on the patient associated with operation. In addition, an advanced technique is required for an operator. Implant once implanted sometimes cannot be removed or exchanged when they have become unnecessary. Further, the drug dispersed in the vitreous body is metabolized and subjected to the control of substance permeation by the inner limiting membrane (ILM), the outer limiting membrane (OLM), and the blood-retinal barrier; thus, the amount of the drug reaching the retina and the choroid is estimated to be several percent or less, which may reduce the therapeutic effect thereof.

To solve these problems, a less invasive transscleral DDS not requiring vitreous surgery using implantation on the scleral side is devised. The ability of by-passing the above-described ILM, OLM, and blood-retinal barrier by periocular drug delivery can increase the drug concentration in the retina compared to that for the intravitreal slow release, enables local delivery to posterior eye segment tissue, and can minimize side effects due to systemic administration. The sclera is easily permeated by a water-soluble substance, has reduced binding and adsorption of protease and protein, and has low cell density; thus, the drug readily permeates thereinto without receiving metabolism. For example, when albumin is intraocularly injected into the suprachoroid, it is known to be discharged outside the eye through the sclera (see Non Patent Literature 1). Examples of the transscleral DDS are as follows.

1. Transscleral DDS

For example, "transscleral slow-release drug-targeted delivery to the retina and the choroid" is disclosed as a transscleral DDS (see Patent Literature 4). This uses a mechanical osmotic pump (ALZET, ALZA, Palo Alto, Calif.) as a DDS. The osmotic pump takes the form of being subcutaneously buried between the blade bones and transsclerally delivering a drug via a hose extending therefrom; however, the device is complicated and invasive because of implantation in the two areas of the blade bone and the sclera, which is not practical.

For example, "a non-invasive drug delivery system to posterior eye segment tissue using a gel-like composition" is disclosed as a transscleral DDS (see Patent Literature 5). This is a DDS for locally administering a drug to posterior eye segment tissue by administering a gel-like composition comprising the drug and a mucoadhesive substance to the eye surface. However, the gel-like composition is predicted to be readily dispersed to the periphery of an administration site after administration and becomes less effective because it comprises a water-soluble polymer component, and further has a problem that all of the gel-like composition cannot be recovered when it is made redundant.

For example, "an ophthalmologic drug-feeding device" is disclosed as a transscleral DDS (see Patent Literature 6). This is directed to provide an ophthalmic device which can be stably disposed in the eye, is comfortable, and has enough volume and mass to feed a drug for a long period of time. It is a device comprising a silicone elastomer having a curved surface and taper so as to fit on the sclera. The device itself is as large as 10 to 25 mm in width, 5 to 12 mm in height, and 1 to 3 mm in thickness. Its capability of slowly releasing a drug is not disclosed. The device is intended to be inserted into the anterior eye surface and not intended to release a drug to posterior eye segment tissue.

For example, "transscleral delivery" is disclosed as a transscleral DDS (see Patent Literature 7). This is a DDS intended for the delivery of rapamycin to posterior eye segment tissue. The subscleral injection of microspheres/nanoparticles, the scleral surface implantation of a biodegradable polymer as a thin layer membrane having an impervious lining, the implantation thereof in a surgically formed scleral pocket, the implantation of a solid core of drug in the scleral pocket, and the insertion of a silicone track delivery system into the recti tendon are disclosed as a delivery system. A method involving using a specially designed injector/inserting device and inhibiting the movement of DDS by employing a suture or attaching a fine needle to DDS itself in order to secure DDS is disclosed as an insertion method. An effective concentration of rapamycin is shown to permeate by preparing an in vitro scleral model in which a human donor sclera is mounted in a chamber to evaluate the permeability of rapamycin; however, the period of slow release is not clearly indicated.

As described above, the transscleral DDSs previously reported have had a problem that they are complex systems, have fluidity, cause a feeling of a foreign body because of their large size, or have a short period of slow release.

Collagen and polyethylene glycol (PEG) have conventionally been used as base materials for DDS. Collagen is a protein of biological origin and functions as an extracellular matrix in a living body to regulate the proliferation and differentiation of cells. Due to such biological properties, it is used as a biomaterial for tissue engineering or regenerative medicine. More recently, it is clinically applied to an injectable filler, a hemostatic agent, an artificial skin, or the like. PEG is a biocompatible synthetic polymer which is nontoxic and exhibits reduced interaction with a living body. It is also subjected to clinical applications in the medical field, including the stabilization of a protein drug in a living body by pegylation such as use as an emulsifier for cosmetics. Examples of materials for treating the eye using collagen and PEG are as follows.

2. Collagen DDS

For example, "a suspension for treating the eye" is disclosed as a material for treating the eye using collagen (see Patent Literature 8). This is directed to provide an artificial tear solution for preventing the drying of the eye surface, and comprises a mixture of biodegradable particles (collagen, gelatin, etc.) 0.5 mm in diameter, an ophthalmologic drug, and a lipid-like substance; it is intended for treating the eye surface and is not a DDS intended for intraocular therapy.

For example, "an injectable collagen-based drug delivery preparation and its use" is disclosed as a material for treating the eye using collagen (see Patent Literature 9). This is directed to provide a subcutaneous injection-type drug delivery carrier, and is a DDS in which a mixture of atelocollagen, a drug, and a cross-linking agent is subcutaneously injected and then cross-linked in situ for solidification. The target disease therefor is not described. However, the in situ cross-linking is unfavorable because the unreacted cross-linking agent may induce an inflammatory response in the biotissue.

For example, "an optically clear ultraviolet-absorbing biocompatible polymer material using collagen as a base material and a method for producing the same" is disclosed as a material for treating the eye using collagen (see Patent Literature 10). This is intended for producing an intraocular lens and a contact lens, and a hydrophilic or hydrophobic acrylic monomer and allyl monomer are graft-polymerized with collagen in order to obtain transparency and ultraviolet absorptivity. A material comprising a composite of collagen and PEG is exemplified; it is not intended for intraocular therapy because it is not packed with a drug.

For example, "a collagen gel and a method for producing the same" is disclosed as a DDS using collagen (see Patent Literature 11). This describes a method for producing a collagen gel, which involves mixing a cross-linking agent in the process of fiber formation of collagen and causing the fiber formation and the cross-linking to occur simultaneously. A DDS is disclosed which uses a dry collagen sheet obtained by removing a solvent in the collagen gel; however, examples thereof are not described and the slow-releasing capability and use thereof are unknown.

As described above, for a material for treating the eye using collagen, a transscleral DDS is not disclosed which is intended for drug delivery to posterior eye segment tissue.

3. Pegylated DDS

For example, "an injection for intraocular tissue comprising a drug-polyethylene glycol conjugate" is disclosed as a material for treating the eye using PEG (see Patent Literature 12). The injection exploits the failure of the drug conjugated to PEG to transfer to the systemic circulation when directly injected into the eye because it has a larger apparent molecular weight, and is intended for the intraocular stabilization of the drug by PEG. However, it depends on the dispersion of the intraocularly injected drug whether the drug is transferred to a target site, and, as described above, the drug suffers from permeation inhibition by the ILM, OLM, and blood-retinal barrier; thus, the arrival rate of the drug at posterior eye segment tissue is several percent or less, posing a problem that the therapeutic effect thereof is decreased.

For example, "an ophthalmic drug delivery system using polymer micelles" is disclosed as a material for treating the eye using PEG (see Patent Literature 13). This is a method which involves including a light-sensitive substance used for photodynamic therapy (PDT) in micelles each using PEG as an outer shell and polyaspartic acid (Asp) as an inner shell and using the resultant for PDT. The use of this method enables the effective delivery of the light-sensitive substance to the posterior eye segment tissue producing vascularization and can block the vascularization using a low level of laser irradiation. However, depending on the disease state, it is necessary to repeatedly maintain the laser irradiation, posing a problem of side effects of the laser irradiation on the eye tissue.

As described above, for a material for treating the eye using PEG, a transscleral DDS is not disclosed which is intended for drug delivery to posterior eye segment tissue.

CITATION LIST

Patent Literature

Patent Literature 1: JP Patent Publication (Kokai) No. 06-312943
Patent Literature 2: JP Patent Publication (Kohyo) No. 2008-535847
Patent Literature 3: JP Patent Publication (Kohyo) No. 2008-520547
Patent Literature 4: JP Patent Publication (Kohyo) No. 2002-534139
Patent Literature 5: JP Patent Publication (Kokai) No. 2007-56014
Patent Literature 6: JP Patent Publication (Kohyo) No. 2007-503265
Patent Literature 7: JP Patent Publication (Kohyo) No. 2007-505932
Patent Literature 8: JP Patent Publication (Kokai) No. 04-1124
Patent Literature 9: JP Patent Publication (Kokai) No. 08-34747
Patent Literature 10: JP Patent Publication (Kohyo) No. 2002-528043
Patent Literature 11: JP Patent No. 4064435
Patent Literature 12: JP Patent Publication (Kokai) No. 2003-171315
Patent Literature 13: JP Patent Publication (Kokai) No. 2005-8614

Non Patent Literature

Non Patent Literature 1: Arch. Opthalmol. 74, 248-52, 1995

SUMMARY OF INVENTION

Although DDS is intended for "feeding a minimum necessary drug to where the demand is when needed", the site of the implantation thereof has been limited by the inadequate shape/size of DDS, posing a problem that the drug reaches a non-target site to cause side effects. The use of DDS has also sometimes been accompanied by an inflammatory response derived from the base material of DDS. In addition, some conventional DDSs have produced the initial burst to initially release an excessive amount of a drug or have had an insufficient period of slow release.

For a DDS for treating eye disease, a method is disclosed which involves surgically administrating/implanting a DDS carrier and a drug through the vitreous body to the subretina; however, this method places a heavy physical/economic burden on patients, also poses a high risk of infection, and sometimes requires an operator to have an advanced technique. The DDS carrier thus administered is most often difficult to remove when it is made redundant or when it produces side effects. As a method for solving this problem, some transscleral DDSs are disclosed; however, they have had a problem that they are complex systems, have fluidity, cause a feeling of a foreign body because of their large size, or have a short period of slow release.

An object of the present invention is to provide a DDS for solving the above problems, which can be safely and simply implanted into the eye and can deliver a drug into the eye over a long period of time without the initial burst, particularly in application to the treatment of eye disease. Another object thereof is to provide a highly versatile long-term slow-release DDS also capable of being applied to organs/tissues other than the eye.

As described above, the DDSs previously disclosed have had a problem that it is inappropriate in the biocompatibility and shape, cannot achieve stable drug release due to the production of the initial burst, or has a short period of slow release. Particularly, the DDSs for intraocular therapy have had a problem that they are complex systems, have fluidity, cause a feeling of a foreign body because of their large size, or have a short period of slow release.

To solve these problems, the present inventors have made extensive studies, aiming at development of a compact-size stepwise slow-releasing transscleral DDS capable of unidirectionally delivering a therapeutic level of a drug to the choroid and the retina for a long period of time without damage to tissue.

The present inventors have used collagen and PEG as base materials for DDS. The present inventors have developed a drug reservoir capsule 1 mm or less in thickness and 1 $cm^2$ or less in area to facilitate insertion into the sclera (the sclera as used herein refers to the range from above the choroid to under the conjunctiva, that is, the subsclera, the inside of the sclera, the episclera, the subconjunctiva, and the suprachoroid). The capsule has been produced by capping a box-shaped reservoir prepared from PEG with a porous PEG sheet. The porous PEG sheet has been produced by collagenase digestion using collagen particles as a porogen (a porous mold). The change of the mixing amount of collagen particles can change the pore density. As a result, it has been found that the permeability/slow-release capability of a drug in the capsule can be easily controlled. In addition, it has been found that the drug can be packed in the capsule not in the form of a common solution but in the form of the drug impregnated in collagen (the form of collagen may be a gel or particles) or the resultant collagen wrapped in PEG and pelletized to promote slow release. In other words, this is a new DDS concept of 2 step slow release according to which the slow release of the drug from the collagen occurs in the capsule and the drug is further slowly released through the porous sheet. The combination of the method for packing the drug in the capsule and the porosity of the porous PEG sheet has enabled the period of slow release of 5 years or more to be achieved. In addition, it has been found that the inside of a capsule can be compartmented using a fine processing technology to pack several drugs and the change of the packing form enables the slow release of several drugs at different speeds. Animal experiments have showed that a drug is slowly released in a sustained manner from the device implanted on the sclera.

Thus, a scleral DDS has been developed which can slowly release a drug for a longer period of time than that for a conventional technique, is easily inserted into the sclera, and can slowly release several drugs at different speeds, thereby accomplishing the present invention.

Thus, the present invention is as follows.
[1] A sustained drug delivery system in which an implant is implanted in the body, wherein the implant is a polyethylene glycol (PEG) capsule having a structure in which a box-shaped PEG internally containing a collagen impregnated with a therapeutic drug or a PEG pellet including the collagen impregnated with a therapeutic drug is capped with a porous PEG sheet and the internal drug is slowly released through the porous PEG sheet.

[2] The sustained drug delivery system according to [1], wherein the system is a stepwise slow-releasing drug delivery system in which the collagen impregnated with a therapeutic drug or the PEG pellet including the collagen impregnated with a therapeutic drug is internally contained in the box-shaped PEG.

[3] The sustained drug delivery system according to [1] or [2], wherein the therapeutic drug is in the form of a solution, powdered particles, or a mixture thereof.

[4] The sustained drug delivery system according to any of [1] to [3], wherein the collagen impregnated with a therapeutic drug is in the form of a collagen gel or collagen particles.

[5] The sustained drug delivery system according to any of [1] to [4], wherein the PEG pellet in which the collagen impregnated with a therapeutic drug is embedded is prepared by mixing the collagen impregnated with a drug, a photo-curable polyethylene glycol, and a photopolymerization initiator and curing the mixture.

[6] The sustained drug delivery system according to any of [1] to [5], wherein the box-shaped PEG is prepared by mixing a photo-curable polyethylene glycol and a photopolymerization initiator and curing the mixture with UV light.

[7] The sustained drug delivery system according to any of [1] to [6], wherein the porous PEG sheet is prepared by a photo-curable polyethylene glycol solution, collagen particles, and a photopolymerization initiator, irradiating the mixture with UV light for curing, and then digesting the collagen particles.

[8] The sustained drug delivery system according to any of [5] to [7], wherein the photo-curable polyethylene glycol is selected from the group consisting of polyethylene glycol dimethacrylate (PEGDM), polyethylene glycol methacrylate (PEGMA), and polyethylene glycol diacrylate (PEGDA).

[9] The sustained drug delivery system according to any of [1] to [8], wherein the system is a sustained drug delivery system for treating eye disease in which an implant for administering a drug for treating eye disease in a sustained manner is implanted in a portion from above the choroid to under the conjunctiva, that is, the subsclera, the inside of the sclera, the episclera, the subconjunctiva, and the suprachoroid.

[10] The sustained drug delivery system according to [9], wherein the eye disease is a disease in which multiple factors including a gene and an environmental factor are involved, a retinal blood vessel lesion, or a disease in which inflammation or damage spreads to the choroid/retina/vitreous body.

[11] The sustained drug delivery system according to [10], wherein the disease in which multiple factors including a gene and an environmental factor are involved is selected from the group consisting of retinal pigmentary degeneration, age-related macular degeneration, and glaucoma; the retinal blood vessel lesion is selected from the group consisting of retinal artery occlusion, branch retinal vein occlusion, and diabetic retinopathy; and the disease in which inflammation or damage spreads to the choroid/retina/vitreous body is uveitis.

[12] The sustained drug delivery system according to any of [1] to [11], wherein the therapeutic drug is selected from the group consisting of a drug suppressing vascularization, a drug promoting the growth of nerve cells, a steroid drug, a therapeutic drug for glaucoma, an anti-inflammatory drug, an antifungal drug, and an anticancer drug.

[13] A drug slow-releasing implant, wherein the implant is a PEG capsule having a structure in which a box-shaped PEG internally containing a therapeutic drug, a collagen impregnated with the therapeutic drug, or a PEG pellet in which the collagen impregnated with the therapeutic drug is embedded is capped with a porous PEG sheet and the internal drug is slowly released through the porous PEG sheet.

[14] The drug slow-releasing implant according to [13], wherein the implant is a stepwise slow-releasing implant in which the collagen impregnated with the therapeutic drug or the PEG pellet in which the collagen impregnated with the therapeutic drug is embedded is internally contained in the box-shaped PEG.

[15] The drug slow-releasing implant according to [13] or [14], wherein the therapeutic drug for impregnation is in the form of a solution, powdered particles, or a mixture thereof.

[16] The drug slow-releasing implant according to any of [13] to [15], wherein the collagen impregnated with the therapeutic drug is in the form of a collagen gel or collagen particles.

[17] The drug slow-releasing implant according to any of [13] to [16], wherein the PEG pellet in which the collagen impregnated with the therapeutic drug is embedded is prepared by mixing the collagen impregnated with the drug, a photo-curable polyethylene glycol, and a photopolymerization initiator and curing the mixture with UV light.

[18] The drug slow-releasing implant according to any of [13] to [17], wherein the box-shaped PEG is prepared by mixing a photo-curable polyethylene glycol and a photopolymerization initiator and curing the mixture with UV light.

[19] The drug slow-releasing implant according to any of [13] to [18], wherein the porous PEG sheet is prepared by mixing a photo-curable polyethylene glycol solution, collagen particles, and a photopolymerization initiator, irradiating the mixture with UV light for curing, and then digesting the collagen particles.

[20] The drug slow-releasing implant according to any of [17] to [19], wherein the photo-curable polyethylene glycol is selected from the group consisting of polyethylene glycol dimethacrylate (PEGDM), polyethylene glycol methacrylate (PEGMA), and polyethylene glycol diacrylate (PEGDA).

[21] The drug slow-releasing implant according to any of [13] to [20], wherein the implant is for treating eye disease and implanted in the sclera that is a portion from above the choroid to under the conjunctiva, that is, the subsclera, the inside of the sclera, the episclera, the subconjunctiva, and the suprachoroid.

[22] The drug slow-releasing implant according to [21], wherein the eye disease is a disease in which multiple factors including a gene and an environmental factor are involved, a retinal blood vessel lesion, or a disease in which inflammation or damage spreads to the choroid/retina/vitreous body.

[23] The drug slow-releasing implant according to [22], wherein the disease in which multiple factors including a gene and an environmental factor are involved is selected from the group consisting of retinal pigmentary degeneration, age-related macular degeneration, and glaucoma; the retinal blood vessel lesion is selected from the group consisting of retinal artery occlusion, branch retinal vein occlusion, and diabetic retinopathy; and the disease in which inflammation or damage spreads to the choroid/retina/vitreous body is uveitis.

[24] The drug slow-releasing implant according to any of [14] to [23], wherein it is selected from the group consisting of a drug suppressing vascularization, a drug promoting the growth of nerve cells, a drug promoting vascularization, a steroid drug, a therapeutic drug for glaucoma, an anti-inflammatory drug, an antifungal drug, and an anticancer drug.

The present specification encompasses the contents of the specification and/or drawings of Japanese Patent Application No. 2009-189462 on which the priority of the present application is based.

BRIEF DESCRIPTION OF DRAWINGS

FIG. 2 is a schematic representation of a PEG capsule packed with a drug solution, a collagen gel impregnated with a drug, collagen particles impregnated with a drug, or a PEG pellet of a collagen impregnated with a drug.

FIG. 12 is a graph showing a comparison of the slow-releasing capabilities of 1 step slow release DDS (Coll-FD40 and PEGDM/Col-FD40) and 2 step slow release DDS (PEGDM/Coll-FD40+porous PEGDM sheet).

FIG. 13A-1 is a photograph showing a structure of an arrayed PEG capsule.

FIG. 13A-2 is a schematic diagram showing a structure of an arrayed PEG capsule; a view in top plan thereof and a side view thereof are shown.

FIG. 13A-3 is a photograph showing structures of PEG capsules each having a plurality of compartments. (1/2)

FIG. 13A-4 is a photograph showing structures of PEG capsules each having a plurality of compartments. (2/2)

FIG. 13B-1 is a photograph showing a structure of a PEG capsule alone.

FIG. 13B-2 is a schematic diagram showing a structure of a PEG capsule alone; a view in top plan thereof and a side view thereof are shown.

FIG. 17A shows a combination of a PEG sheet and a PEG box, and FIG. 17B shows a combination of a PEG sheet prepared into a box shape and a PEG box.

FIG. 18A shows a PEG box having a suture hole, and FIG. 18B is a PEG box whose corners were removed to permit crosswise suture.

FIG. 21A is a visible photograph before photographing fluorescence, and FIGS. 21B to E are photofluorograms 1 week, 2 weeks, 3 weeks and 5 weeks, respectively, after implantation. In FIGS. 21B to E, the white portions indicate fluorescence.

FIG. 22A shows the distribution of fluorescein, and FIG. 22B shows the distribution of FD40. In the figure, SC indicates the sclera, RP, the retinal pigment epithelium, and RE, the retina.

FIG. 24A shows the side of a PEG box, and FIG. 24B shows the side of a porous PEG sheet.

DESCRIPTION OF EMBODIMENTS

Figure 1:
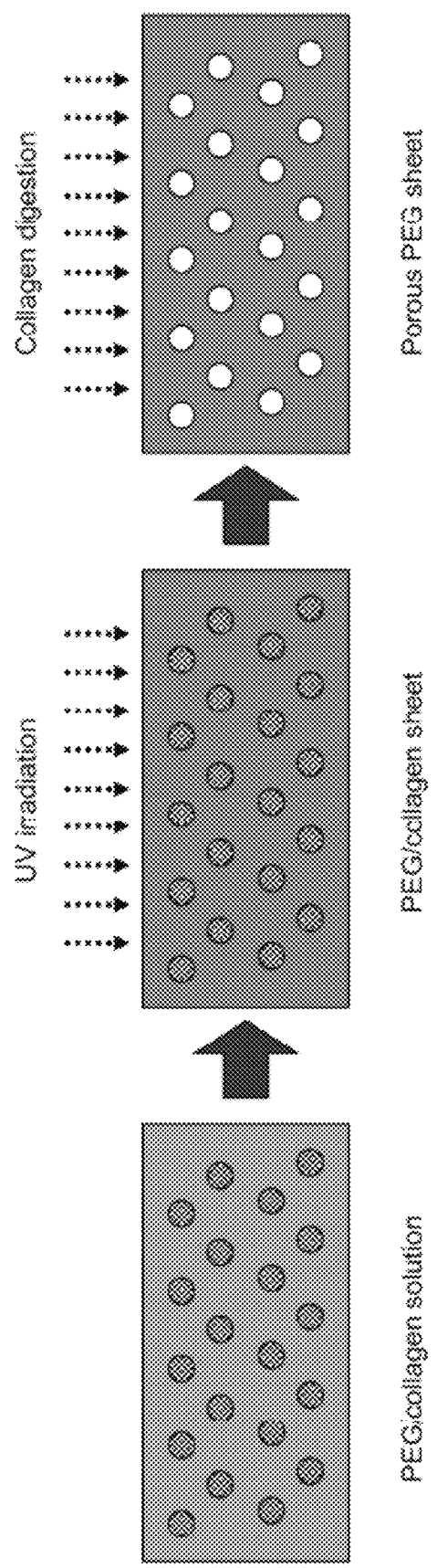
FIG. 1 is a flow diagram summarizing a method for producing a porous PEG sheet.

The present invention will be described below in detail.

The therapeutic drug reservoir capsule used in the sustained DDS of the present invention consists of a PEG-made box-shaped reservoir and a porous PEG sheet, and has a capsule structure in which the box-shaped reservoir is closed by a cap made of a sheet-like or box-shaped porous PEG sheet.

The box-shaped reservoir contains a collagen impregnated with a therapeutic drug or the collagen impregnated with a drug included in PEG and pelletized. As used herein, the form of collagen may be a gel or particles. The drug may be placed in the form of a solution or powder or in the form of a mixture thereof, and the drug may be packed in various forms for applications. The collage impregnated with a drug is also referred to as a drug-embedded collagen or a collagen containing a drug.

The therapeutic drug contained in the capsule is slowly released to the outside through the portion consisting of a porous PEG sheet of the capsule.

Method for Preparing Collagen Gel Impregnated with Drug

The collagen may be any type of collagen and may use, for example, types I to VIII collagen. The origin of collagen is not limited, and collagen derived from a mammal, a bird, a fish, or the like may be used. A recombinant human collagen may also be used. For example, in view of industrial use, preferred is type 1 collagen, obtained in high yield, or a collagen consisting mainly of the collagen. The molecular structure of the collagen used in the present invention is not particularly limited. The collagen may be one having or not having fiber-forming capability. The both ends of a collagen molecule are reported to have telopeptide in the non-helical region, the peptide having antigenicity. Telopeptide should be removed in some applications; however, it may be removed or not removed.

The collagen used in the present invention is not particularly limited in its denaturation. Even collagen once denatured is known to partially restore the helical structure of the collagen. The helical rate can be determined from the specific rotatory power measured using an optical rotatory power meter; however, its helical rate is not particularly limited.

Collagen is divided mainly into acid-solubilized collagen, extracted with an acid aqueous solution, and alkali-solubilized collagen, extracted with an alkali aqueous solution. It is not particularly limited; however, an acid aqueous solution of collagen is preferable.

The solvent of a collagen solution is preferably water, which is safe and widely used for industrial applications, or an aqueous solution of hydrochloric acid, citric acid, fumaric acid, or the like for an acidic solvent in view of final applications. For a neutral to alkaline solvent, it is preferably water, or an aqueous solution of a phosphate, an acetate, Tris, or the like from the same reason described above.

The method for preparing a collagen gel is not particularly limited provided that it is such a processing method that collagen gelates by losing fluidity; however, it is preferable in the present invention to use a method involving mixing a solvent containing a cross-linking agent in a collagen solution and a method involving mixing a solvent causing the fiber formation of collagen therein. The addition of a cross-linking agent to a collagen solution results in the gelation of the collagen solution by the cross-linking of collagen molecules. When a buffer having a buffer capacity is mixed to the collagen solution to make the pH near neutral, collagen molecules are self-assembled to form collagen fibers to form a hydrogel. A drug can be mixed in the gelation of collagen to prepare a collagen gel impregnated with the drug. Here, the drug may be in the form of powder or a solution. In the case of a solution, it is recommended that the drug be dissolved in a solvent used for gelation.

The concentration of collagen in the collagen gel is not particularly limited; the gel may be prepared in the range of 0.001% (w/v) to 50% (w/v). A higher concentration of collagen also slows the slow-release of the drug because it reduces the diffusion speed of the solvent.

The buffer used for the gelation of collagen is not particularly limited provided that it is a solvent causing the fiber formation of collagen. However, considering medical materials as final applications, it is preferable to use a salt aqueous solution having a buffer capacity such as a phosphate, an acetate, a carbonate, or Tris, which has no or low cytotoxicity and is widely used for industrial applications. The pH suitable for the fiber formation of collagen varies depending on the type of collagen; however, it is often in the range of pH 5 to 9; and a phosphate, which has a high buffer capacity in the range, is particularly preferably used.

The temperature when collagen is subjected to fiber formation may be a lower temperature than the denaturation temperature of the collagen used. A higher temperature than the denaturation temperature may denaturate collagen to cause no fiber formation. Particularly, collagen derived from a mammal such as a cow or a pig easily causes fiber formation at about 37° C. and less easily causes fiber formation at a temperature lower than 20° C. Thus, to uniformly impregnate a drug in a collagen gel, the drug may be mixed at 20° C. or less, followed by placing the mixture an incubator at 37° C. for gelation.

The cross-linking agent used for the cross-linking of a collagen solution is not particularly limited provided that it can cross-link a protein and is water-soluble. Among others, aldehyde, carbodiimide, epoxide and imidazole cross-linking agents are preferably used in view of economy, safety, and ease of operation. Particularly, it is preferable to use water-soluble carodiimides such as 1-ethyl-3-(3-dimethylaminopropyl)carbodiimide hydrochloride and 1-cyclohexyl-3-(2-morpholinyl-4-ethyl)carbodiimide sulfonate.

The concentration of the cross-linking agent is not particularly limited. The concentration may be determined depending on the application because the biodegradation rate and slow-release speed of collagen can vary depending on the cross-linking agent concentration. The final concentration is preferably in the range of 0.01 mM to 1 M.

Method for Preparing Collagen Particle Impregnated with Drug

The collagen particle impregnated with a drug (a collagen particle is sometimes referred to as a Coll particle) is the drug impregnated in particulate collagen. The collagen particles impregnated with a drug are prepared by adding the drug into a collagen solution, emulsifying the resultant to form a water-in-oil emulsion internally containing the drug, cross-linking spherical collagen in the emulsion, and preparing cross-linked collagen particles, which are used as the collagen particles impregnated with the drug. Alternatively, they can also be prepared by producing collagen particles in the same way as the above, except for omitting the addition of the drug and then impregnating the collagen particles in a drug solution. Good in the efficiency of impregnation of the drug is the impregnation after cross-linking, in which the collagen particles are prepared and then impregnated in the drug solution.

The pH during the emulsification is not particularly limited and varies depending on the method for producing a collagen raw material. Collagen is divided mainly into acid-solubilized collagen, extracted with an acid aqueous solution, and alkali-solubilized collagen, extracted with an alkali aqueous solution. When the collagen solution used in the present invention is acid-solubilized collagen, its pH during emulsification is preferably 2 to 6. A pH of less than 2 is unfavorable because it may result in the hydrolysis of collagen. When the collagen used in the present invention is alkali-solubilized collagen, its pH is preferably 5.5 to 10. A pH of less than 5.5 may not result in the sufficient solubilization of collagen. A pH of more than 10 is unfavorable because it may result in the hydrolysis of collagen molecules.

The concentration of the collagen solution during emulsification is preferably in the range of 0.01 to 10% (w/v) in view of the solubility of collagen and the viscosity of the solution. More preferred is 0.5 to 2% (w/v).

In the emulsification, an oily liquid organic compound and an emulsifier may be added and mixed in a solution containing a therapeutic drug and collagen. The oily liquid organic compound (the so-called oil) is generally a flammable substance non-miscible with water, and is derived from a plant, an animal, or a mineral; however, it is not particularly limited in the present invention. Examples of the compound which may be used include liquid paraffin, Japan wax, beeswax, rice wax, microcrystalline wax, polyolefin wax, and carbana wax; liquid paraffin is preferable, among others. The emulsifier refers to the so-called surfactant and is not particularly limited provided that it is an amphiphilic molecule; examples thereof which may be used include anionic surfactants, cationic surfactants, amphoteric surfactants, and nonionic surfactants. In the present invention, surfactants such as a sorbitan ester and a polysorbate may be used; preferably, sorbitan monolaurate (Span 20) may be used.

The collagen particles produced by the emulsification are cross-linked using a cross-linking agent. The cross-linking agent is not particularly limited provided that it can cross-link a protein and is water-soluble. Among others, aldehyde, carbodiimide, epoxide and imidazole cross-linking agents are preferably used in view of economy, safety, and ease of operation. Particularly, it is preferable to use water-soluble carodiimides such as 1-ethyl-3-(3-dimethylaminopropyl)carbodiimide hydrochloride and 1-cyclohexyl-3-(2-morpholinyl-4-ethyl)carbodiimide sulfonate.

The concentration of the cross-linking agent is not particularly limited. The concentration may be determined depending on the application because the biodegradation rate and slow-release speed of collagen can vary depending on the cross-linking agent concentration. The final concentration is preferably in the range of 0.01 mM to 1 M.

In the emulsification, a solvent causing the fiber formation of collagen may be mixed. For example, a salt aqueous solution having a buffer capacity such as a phosphate, an acetate, a carbonate, or Tris, which is widely used for industrial applications, may be mixed in advance.

The temperature during emulsification varies depending on the denaturation temperature of the collagen raw material used. For example, cow- or pig-derived collagen has a denaturation temperature of 37 to 40° C. and thus is preferably emulsified at a temperature lower than the temperature range.

The average particle diameter of the collagen particles impregnated with a drug is 0.01 to 200 μm, preferably 5 to 10 μm.

The collagen particles can be produced by the method described in the example to be stated later.

Attempts have also been made to use, as a biodegradable carrier for a drug or the like, particles produced by preparing a water-in-oil emulsion (w/o emulsion) using collagen dissolved in an aqueous solvent and cross-linking the emulsion. For example, JP Patent Publication (Kokai) No. 2006-291198 discloses cross-linked collagen spherules obtained by preparing an emulsion in oil using a collagen solution employing an acidic aqueous solvent, recovering the emulsion in the form of collagen spherules, and then cross-linking the spherules, and a method for producing the same. JP Patent Publication (Kohyo) No. 08-502922 discloses microcapsules obtained by preparing an almost homogeneous solution, forming an emulsion in a continuous phase, recovering and washing the emulsion in the form of particles, and cross-linking the resultant, and a method for producing the same.

These methods prepare cross-liked collagen spherules and microcapsules by recovering a w/o emulsion before cross-linking, and are not those which involve cross-linking a w/o emulsion in a continuous phase as in the present invention. No slow release capabilities of the cross-linked collagen spherules and the microcapsules are also described.

During emulsification, collagen may be used in a concentration of 1 to 50% (w/v), preferably 10 to 20% (w/v); the oily liquid organic compound, 50 to 99% (w/v), preferably 80 to 90% (w/v); and the emulsifier, 0.01 to 10% (w/v), preferably 0.1 to 2% (w/v). The addition amount of the therapeutic drug may be properly determined depending on the type of eye disease and the type of the drug.

PEG Pellet

The collagen (in the form of a gel or particles) impregnated with a drug prepared by the above method is included in PEG to prepare a PEG pellet containing the collagen impregnated a drug. The PEG pellet in which the collagen impregnated with a drug is embedded may be mixed with the collagen impregnate with the drug, polyethylene glycol dimethacrylate (PEGDM), and a photopolymerization initiator, placed in a container forming a mold, and cured by irradiation with UV light. Polyethylene glycol methacrylate (PEGMA), polyethylene glycol diacrylate (PEGDA), or the like may be used in place of PEGDM if the PEG is photo-curable PEG. According to the present invention, such photo-curable PEG is sometimes referred to as PEG and expressed as in the form of a PEG pellet, a porous PEG sheet, or a PEG box.

Figure 16:
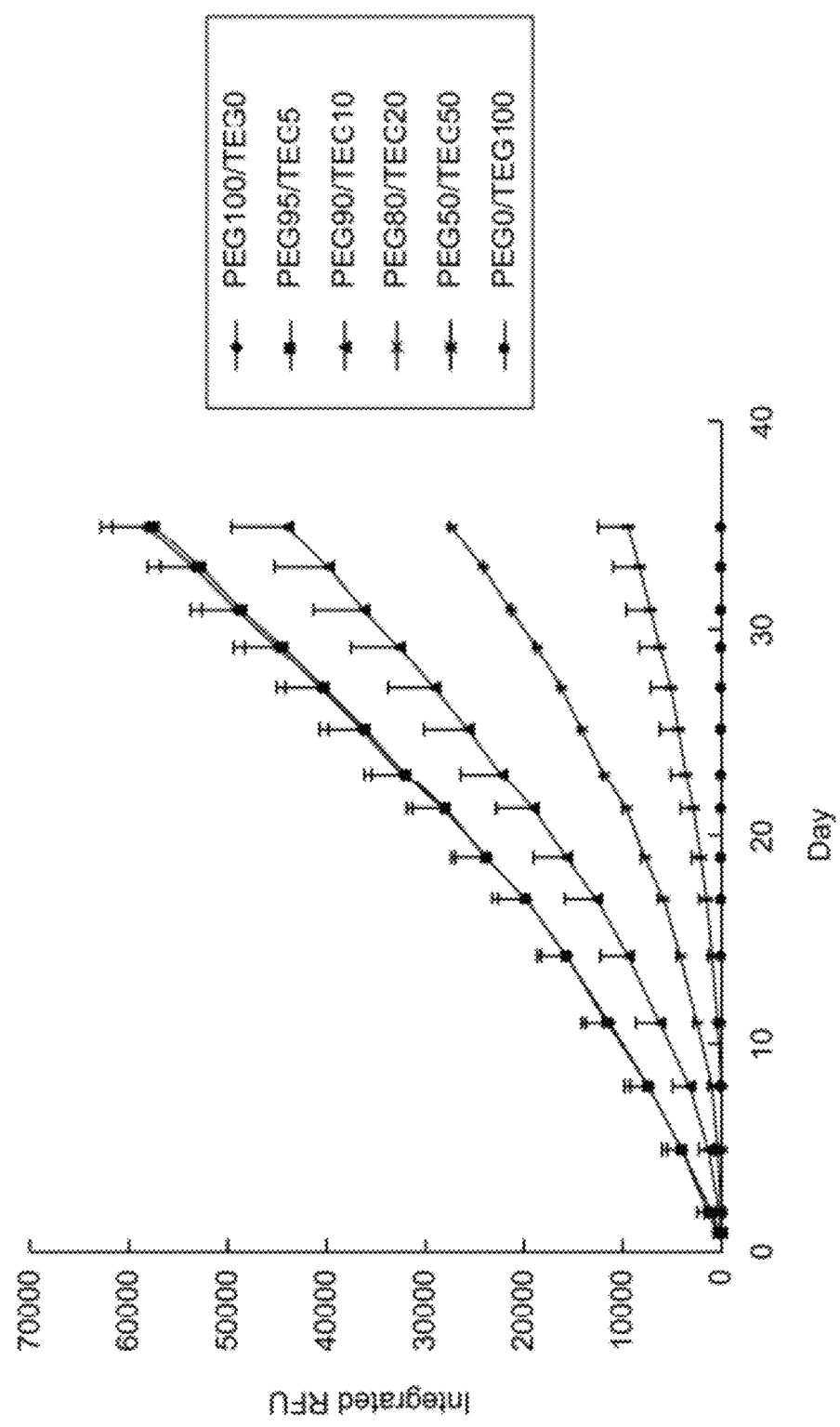
FIG. 16 is a graph showing the slow release of a sodium fluorescein solution from sheets in which PEGDM and TEGDM were mixed at various ratios.

The molecular weight of PEGDM is not particularly limited. As used herein, PEGDM is a polymer in which at least two ethylene glycol monomers are polymerized, and includes low molecular weight PEGDM such as triethylene glycol diacrylate (TEGDM) consisting of 3 monomers or tetraethylene glycol dimethacrylate consisting of 4 monomers. A mixture of PEGDMs having different molecular weights may be used. Thus, the permeability of a drug, particularly the permeability of a low molecular weight drug of 1 kDa or less, can be controlled by the molecular weight of PEGDM in the PEGDM sheet as well as collagen particles. For example, a lower molecular weight monomer results in an increased reduction in the permeability of a drug through a PEG sheet to be described later. Specifically, the mixing of TEGDM (Fw=286.33) and PEGDM (Mn=750) at 100:0 results in almost no drug permeation. On the contrary, the mixing thereof at 0:100 facilitates the permeation of a low molecular weight drug (FIG. 16).

The photopolymerization initiator may properly use a known photopolymerization initiator depending on the wavelength of the light source used. Examples thereof can include 2-hydroxy-2-methyl-propiophenone, 4'-isopropyl-2-hydroxy-2-methyl-propiophenone, 1-hydroxycyclohexyl phenyl ketone, 2,2-diethoxyacetophenone, benzyl methyl ketal, benzyl-β-methoxyethyl acetal, benzoin(2-phenyl-2-hydroxyacetophenone), and benzoin alkyl ether.

On this occasion, for example, a solution of 0.1 to 10 mg/ml, preferably 1 mg/ml of PEGDM and 1 to 100 μg/ml, preferably 10 μg/ml of the photopolymerization initiator may be prepared to mix the solution with the collagen particles impregnated with a drug at a volume ratio of 1:1. The intensity of UV light is 1 to 20 mW/cm$^2$ and the radiation may be carried out for 1 to 5 minutes.

Porous PEG Sheet

The porous PEG sheet is a sheet-like PEG having pores through which a drug can be passed. The porous PEG sheet can be produced by using each of collage particles containing no drug as a porous mold (porogen), mixing a PEGDM solution, collagen particles, and a photopolymerization initiator, irradiating the mixture with UV light for curing, and then digesting the collagen particles using a protease such as collagenase or collagen denaturation treatment by heating. The digestion with an enzyme or the denaturation treatment does not necessarily need to be carried out because collagen particles themselves have the drug permeability. The average molecular weight of the PEGDM used 300 to 6,000, preferably 500 to 1,000 in the case of controlling the permeation of a high molecular weight drug. It is 50 to 6,000, preferably 100 to 1,000 in the case of controlling the permeation of a low molecular weight drug. The average particle diameter of collagen particles used as a porogen may be properly determined depending on the size of the molecular weight of the drug used; however, it is, for example, 0.01 to 200 μm. The photopolymerization initiator may use one described above. When a PEGDM solution and collagen particles are mixed, for example, a solution of 0.1 to 10 mg/ml, preferably 1 mg/ml of PEGDM and 1 to 100 μg/ml, preferably 10 μg/ml of the photopolymerization initiator may be prepared to mix the solution with the collagen particles at a volume ratio of 1:1. On this occasion, a higher concentration of collagen particles increases the density of the particles and also increases the porosity of the porous PEG sheet. The pore size of the porous PEG sheet is preferably 0.01 to 200 µm, and the porosity is 10 to 2,000 pores/cm$^2$. PEGDM is cured by thoroughly stirring the mixed solution to uniformly disperse collagen particles and then irradiating UV light thereon. Thereafter, PEGDM may be immersed in a collagenase solution to digest the collagen particles. PEGDM may be immersed in a solvent at 50° C. or higher to subject the collagen particles to denaturation treatment. The concentration of the collagenase used here is not limited; however, it is, for example, on the order of 1 to 1,000 U/ml. The heating temperature is not particularly limited provided that it is a temperature at which collagen is denatured; however, it is on the order of 40 to 60° C.

On this occasion, molding into sheet form may be performed by production in a container forming a mold for forming a thin membrane. The thickness of the porous PEG sheet is 100 to 1,000 µm.

Figure 17:
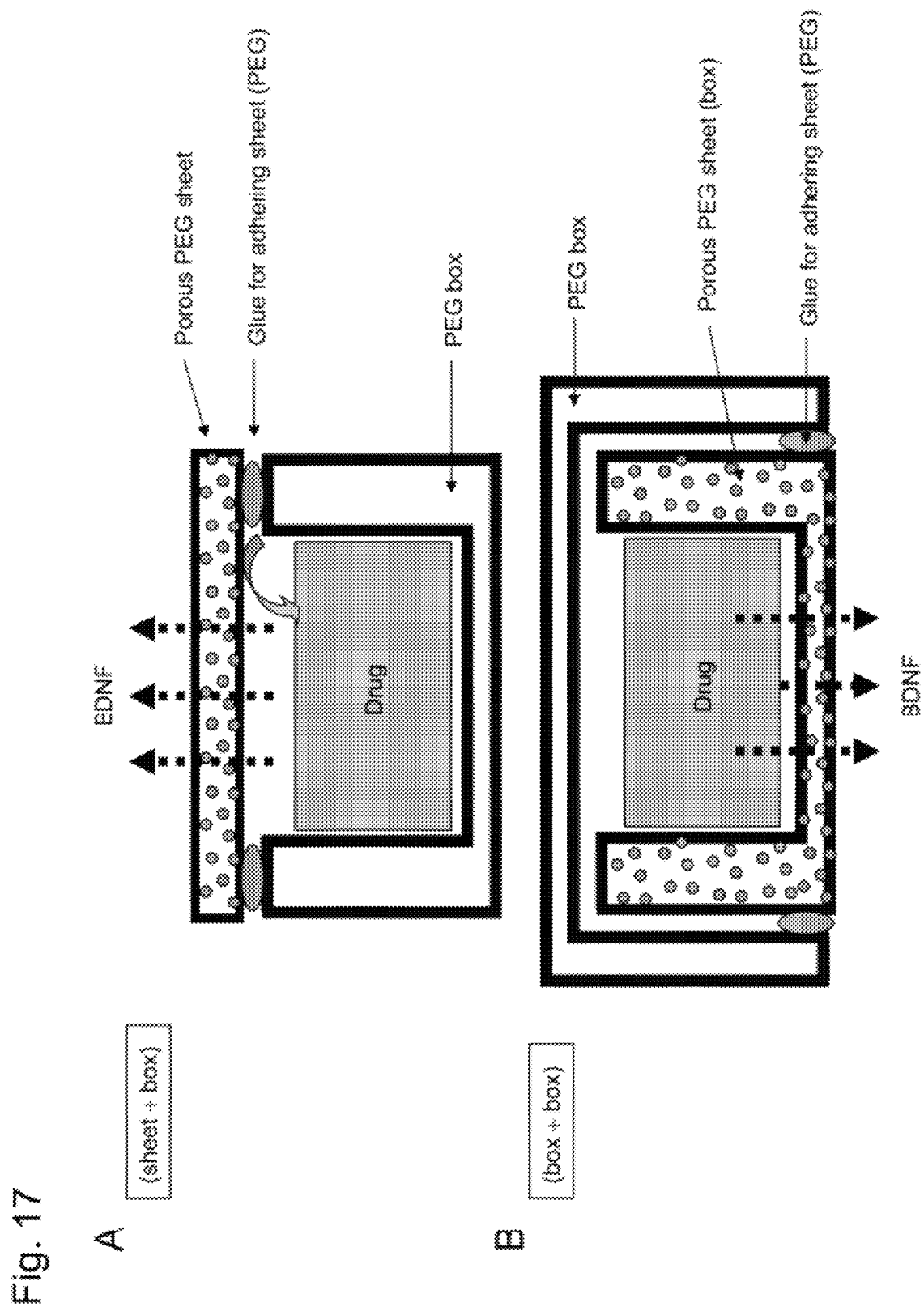
FIG. 17 is a pair of schematic diagrams showing the shapes of PEG capsules.

The porous PEG sheet may be prepared into a box-shape. For example, a box may be prepared so as to provide a bottom thickness of the box of 100 to 1,000 µm, followed by placing a drug therein and then combining the resultant box with a PEG box to be described below (FIG. 17). In the present invention, the box-shaped porous PEG sheet is also referred to as a porous PEG sheet. Both the sheet-like porous PEG sheet and the box-shaped porous PEG sheet function as caps for the PEG box. The box prepared using the porous PEG sheet is sometimes referred to as a slow release box.

The outline of the method for preparing the porous PEG sheet is shown in FIG. 1.

The porous PEG sheet may also be prepared by a known salt leaching method using a salt (JP Patent (Kohyo) No. 2002-541925). According to the salt leaching method, when PEGDM is cured using UV irradiation, sodium chloride particles (NaCl) may be mixed for curing, followed by leaching out and remove NaCl. Microbubbles may also be used as a mold for pores. For example, when a solvent (e.g., water) air-bubbled using Shirasu porous grass membrane (SPG membrane, SPG Technology Co., Ltd) is mixed with PEG and then subjected to UV curing, the air bubbles can become pores to make PEG porous. At this time, the pore size of the SPG membrane can be changed to change the size of the bubbles and thus the size of pores.

PEG Box

The PEG box or the PEG container is PEG processed into a box shape for housing the collagen (a collagen gel or collagen particles) impregnated with a drug, the PEG pellet of the collagen impregnated with a drug, or a drug solution. Here, the box shape refers to a shape capable of internally housing an object, and consists of a bottom and sides. The box-shaped PEG can be prepared by preparing a mold for the box, mixing PEGDM and a photopolymerization initiator in the mold, irradiating the mixture with UV light for curing, and releasing the cured product from the mold. Here, the PEG box refers to a structure made of PEG internally having a recess for housing the collagen (a collagen gel or collagen particles) impregnated with a drug, the PEG pellet of the collagen impregnated with a drug, or a drug solution and having a structure in which the recess can be covered with the above-described porous PEG sheet, and the shape thereof is typically roughly a cube; however, it is not limited thereto and also includes a shape such as a roughly disk-like shape, a roughly spherical shape, or a roughly cylindrical shape. To unidirectionally slowly release a drug, the PEG box is preferably completely impervious to the drug; thus, the PEG box is preferably prepared using TEGDM, which is low molecular weight PEGDM. TEGDM is shown to be completely impervious to a low molecular weight drug (FIG. 16).

PEG Capsule

The collagen (a collagen gel or collagen particles) impregnated with a drug, the PEG pellet of the collagen impregnated with a drug, or a drug solution is placed and packed in the PEG box made of PEG, on which the porous PEG sheet is then put over the opening of the box, followed by irradiating the resultant with UV light to bond the cap made of the porous PEG sheet to the PEG box by light curing to complete a PEG capsule in which the collagen (a collagen gel or collagen particles) impregnated with a drug, the PEG pellet of the collagen impregnated with a drug, or the drug solution is housed in a box-shaped capsule made of PEG. The porous PEG sheet has pores in the cap portion and the internal drug is slowly released through the pores. In other words, the internal drug is slowly released unidirectionally through one side of the box-shaped capsule. Here, the term "capsule" is used to indicate that the collagen (a collagen gel or collagen particles) impregnated with a drug, the PEG pellet of the collagen impregnated with a drug, or the drug solution is sealed by the PEG box and the porous PEG sheet (cap), and the term "capsule" is not intended to limit the structure such as shape. The PEG capsule of the present invention is a box-shaped capsule made of PEG, containing the collagen (a collagen gel or collagen particles) impregnated with a drug, the PEG pellet of the collagen impregnated with a drug, or a drug solution, and the cap of the capsule partially has drug-permeating pores.

In the DDS of the present invention, the collagen impregnated with a drug (a collagen gel or collagen particles) itself has a slow-releasing capability, and the drug is slowly released from the collagen. In the PEG pellet in which the collagen impregnated with a drug is included in PEG, the contact between the collagen and a body fluid is suppressed; thus, the dispersion of the drug in collagen can be further suppressed to prolong the period of slow release. In addition, the packing of the collagen impregnated with a drug or the PEG pellet in which it is included causes the drug to be first slowly released from the collagen or the PEG pellet into the PEG capsule and to be then released to the outside from the PEG capsule through the porous PEG sheet portion. In other words, the DDS of the present invention is a stepwise slow release system in which 2 step slow release occurs. Thus, the DDS of the present invention is a drug reservoir DDS enabling long-term slow release in which the initial burst is suppressed. For example, the impregnation of a drug in collagen particles can decrease the speed of slow release to about 1/5 to 1/20, and the collagen particles can be further made into the form of a PEG pellet to decrease the speed of slow release to about 1/2. The speed of slow release can be measured by the method in the example to be described later.

The size of the PEG capsule can be freely designed; however, considering that it is implanted on the sclera, the size is preferably 1 mm or less in thickness, 5 mm or less in the maximum width, and 1 cm$^2$ or less in the projected area of the widest face.

Figures 1, 13A:
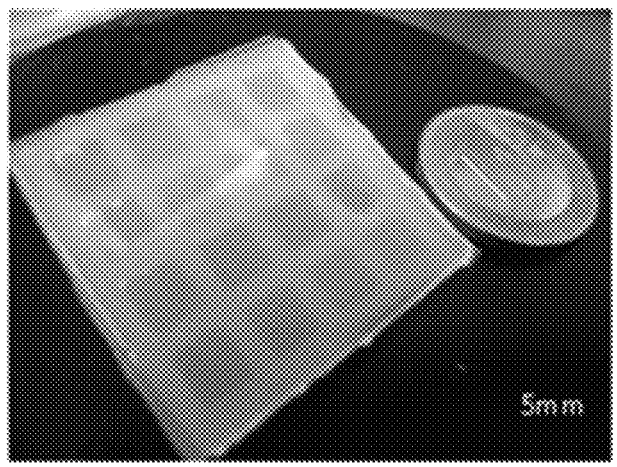
Figures 2, 13A:
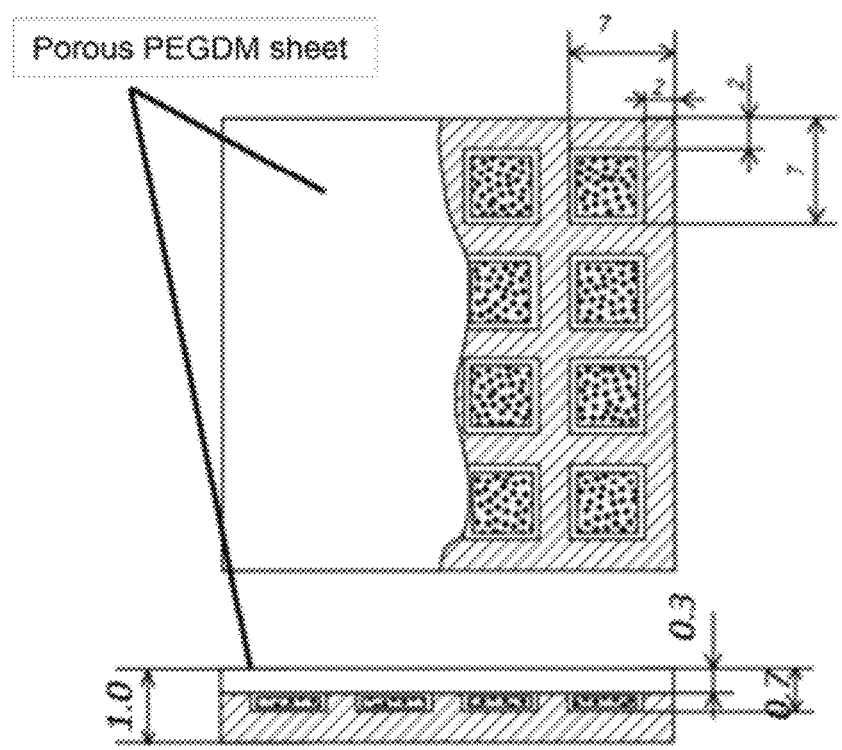
Figures 3, 13A:
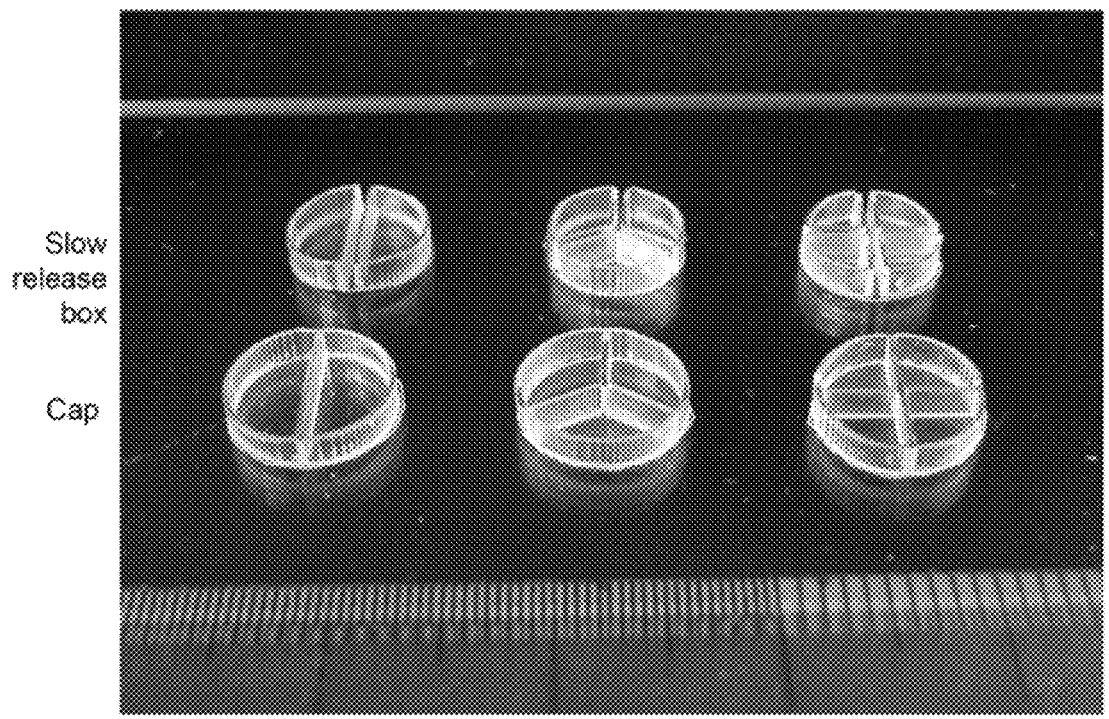
Figures 4, 13A:
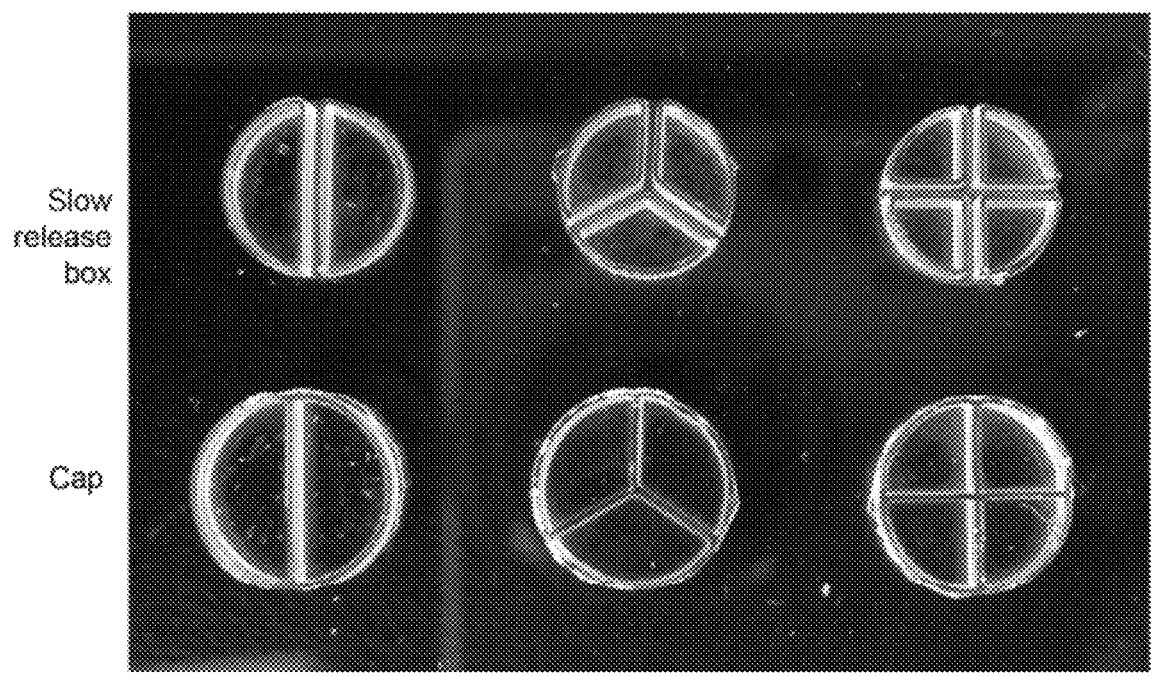

The schematic diagram of the PEG capsule of the present invention is shown in FIGS. 2 and 17. FIGS. 2 and 17A show PGE boxes each covered with a cap made of a porous PGE sheet, and FIG. 17B shows a PEG box covered with a cap made of a box-shaped porous PGE sheet. As shown in FIGS. 17A and B, the PEG box and the porous PEG sheet are bonded using PEGDM as glue.

Figure 3:
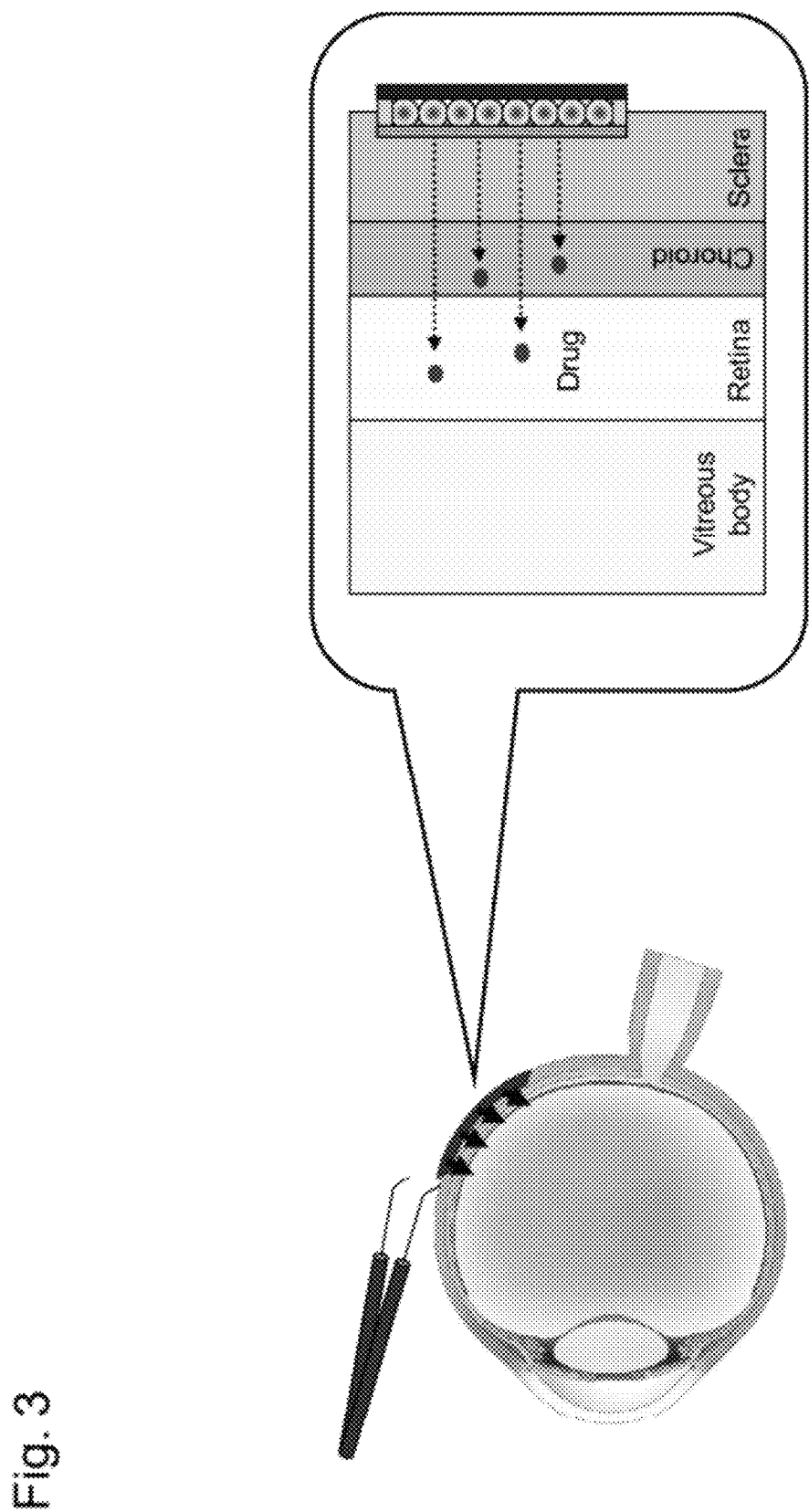
FIG. 3 is a diagram showing the implantation of DDS on the sclera.
Figure 4:
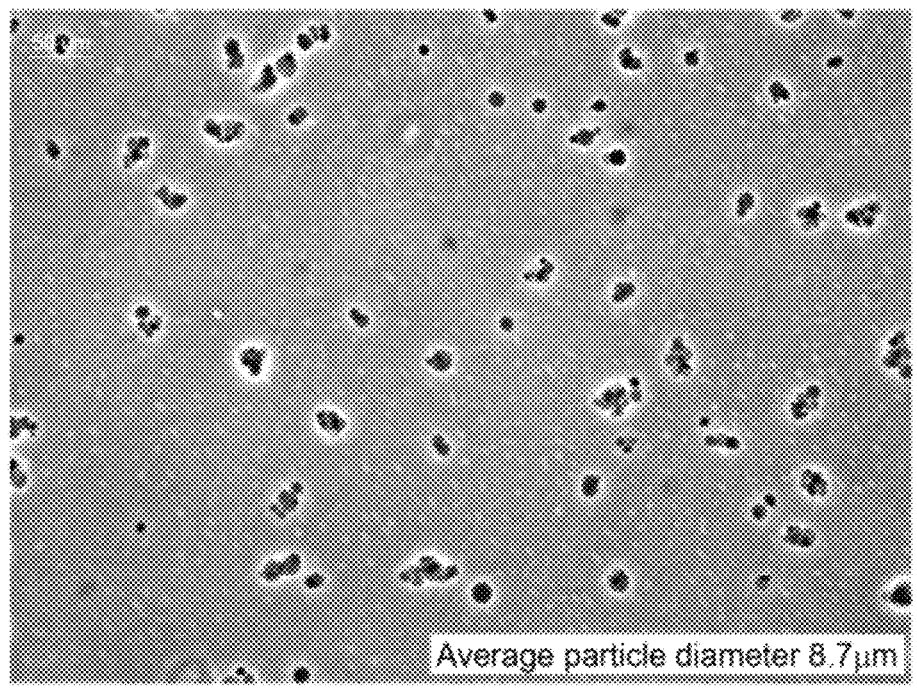
FIG. 4 is a photograph showing a microscopic appearance of collagen particles (Coll particles).

In preparing the PEG box or the box-shaped porous PEG sheet, a plurality of compartments may be provided in the PEG box or the porous PEG sheet. For example, the sheet may be prepared in the form of a PEG sheet in which a plurality of compartments are aligned on an array (FIGS. 13A-1 and 13A-2). The PEG box and the porous PEG sheet may also be produced so that compartments can be delimited. For example, those having 2, 3 and 4 compartments are shown in FIGS. 13A-3 and 13A-4. In FIGS. 13A-3 and 13A-4, box-shaped porous PEG sheets and PEG boxes are shown. The compartmentalization of the inside of the PEG capsule enables a plurality of drugs to be packed in one capsule, enabling the preparation of DDS capable of slowly releasing a plurality of drugs. This is also made possible by separately including drugs of interest when the drugs are included in collagen, followed by insertion into the PEG box. In addition, on this occasion, the packing form of drugs, for example, the way of impregnation in collagen (a collagen gel, collagen particles, etc.) or the way of inclusion in a PEG pellet, can be changed between the drugs to control the individual speeds of slow release of the plurality of drugs, enabling the plurality of drugs to be released at different speeds.

The intended disease of the present invention is not particularly limited; however, examples thereof include a disease for which a drug is desired to be administered in a sustained manner into the body, particularly a disease for which local sustained administration is desired. Examples of the disease include cancer, inflammatory disease, and degenerative disease. Examples thereof also include eye disease; examples of the eye disease include retinal pigmentary degeneration, age-related macular degeneration, glaucoma, and the like in which multiple factors such as a gene and an environmental factor are involved, retinal blood vessel lesions such as retinal artery occlusion, branch retinal vein occlusion, and diabetic retinopathy, and further diseases in which inflammation or damage spreads to the choroid/retina/vitreous body, such as uveitis. Retinal pigmentary degeneration is a disease in which neural retina cells are progressively damaged without any known cause, and listed as an intractable disease (a specified disease). Retinal pigmentary degeneration is an eye disease in which visual cells are progressively degenerated, and visual cells undergo apoptosis (cell death) due to various gene abnormalities, inflammations, immune responses, and the like. Age-related macular degeneration is an eye disease in which new blood vessels and the like appear in the macular area with aging, and a specified disease in which new blood vessels occur from the choroid outside the retina, blood leaks out, and the retina is damaged. Glaucoma is a progressive disease manifested as a characteristic optic disc change and a visual field abnormality. Increased ocular tension was formerly suspected as the cause thereof; however, the vulnerability of the optic disc is suspected as the cause of glaucoma because even many patients having a normal range of ocular tension are identified to suffer from glaucoma. However, increased ocular tension is the biggest risk factor for the progression of glaucoma; the base of treatment of glaucoma is to reduce ocular tension using a drug, and a method for stopping the progression of visual field disturbance is adopted. Glaucoma is top of all causes of vision loss. In addition, retinal artery occlusion, branch retinal vein occlusion, diabetic retinopathy treatment-resistant, and uveitis, which are intractable to treatment, are also contemplated.

Figure 18:
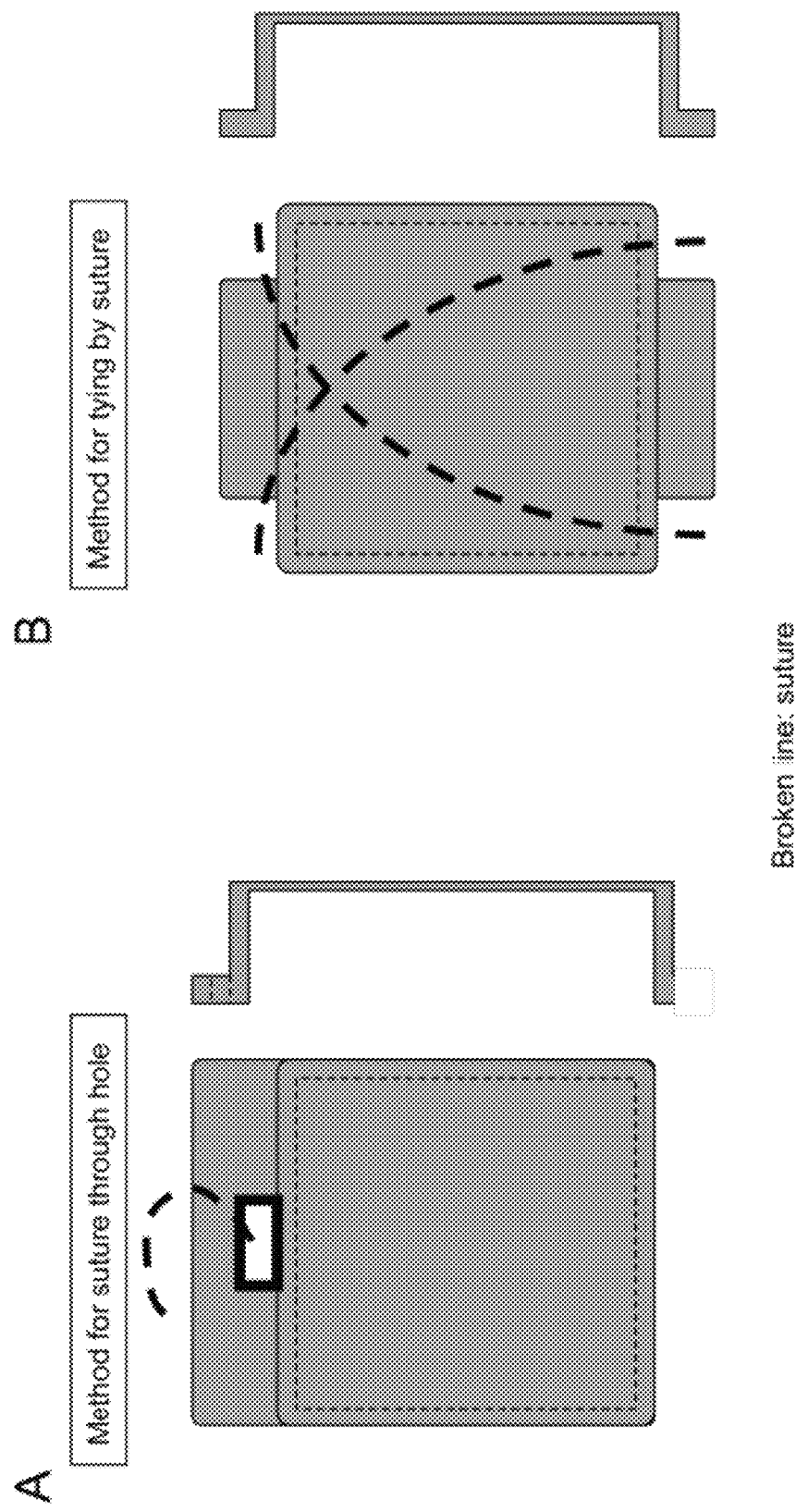
FIG. 18 is a pair of schematic diagrams showing PEG boxes designed to permit fixation on the sclera by suture in implantation.
Figure 19:
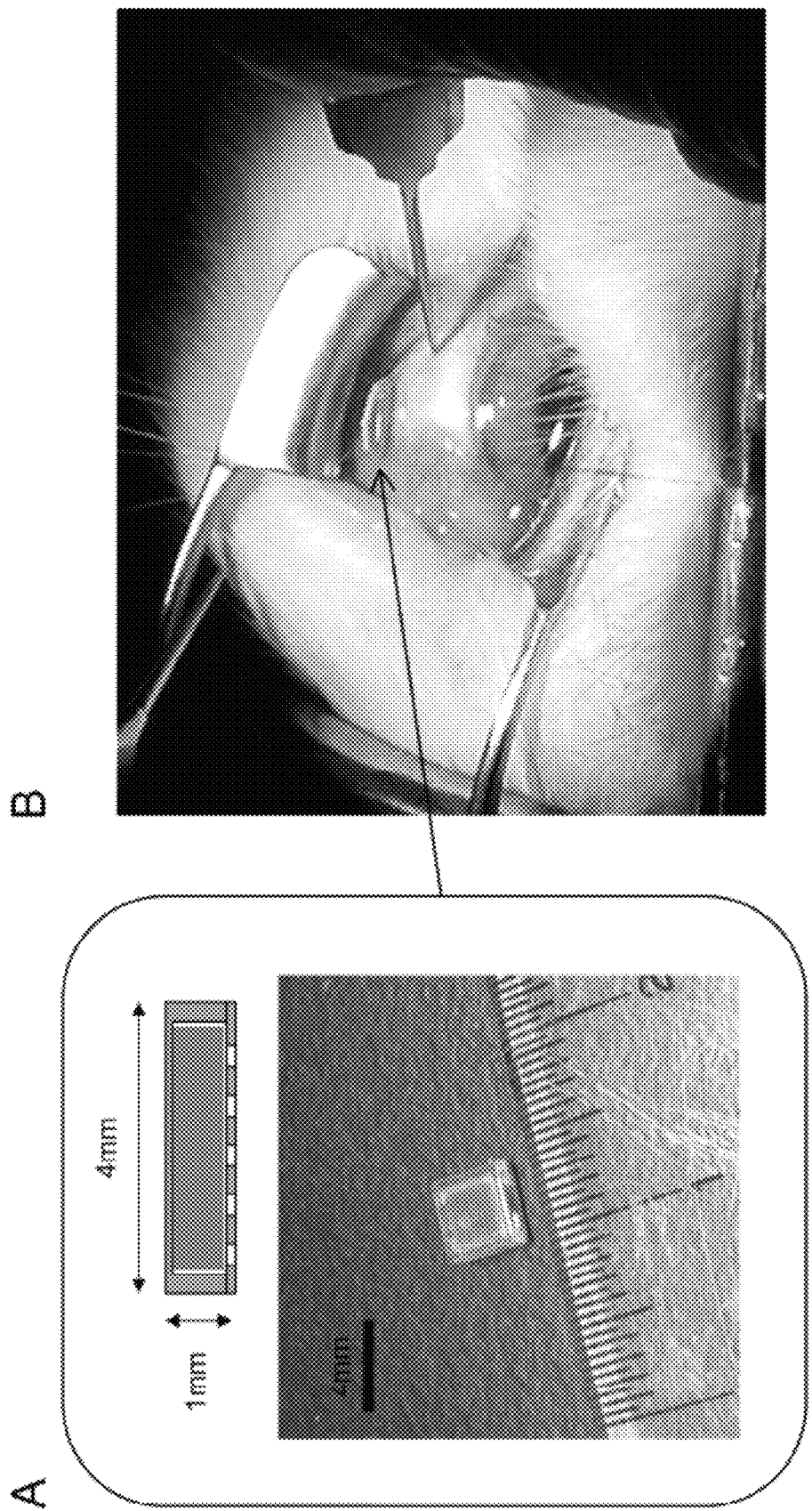
FIG. 19 is a pair of photographs showing a PEG capsule packed with a PEG pellet containing fluorescein (FIG. 19A), and a state immediately after its implantation on the sclera of a rabbit (FIG. 19B). The PEG capsule of FIG. 19A was implanted at the arrow part of FIG. 19B.
Figure 20:
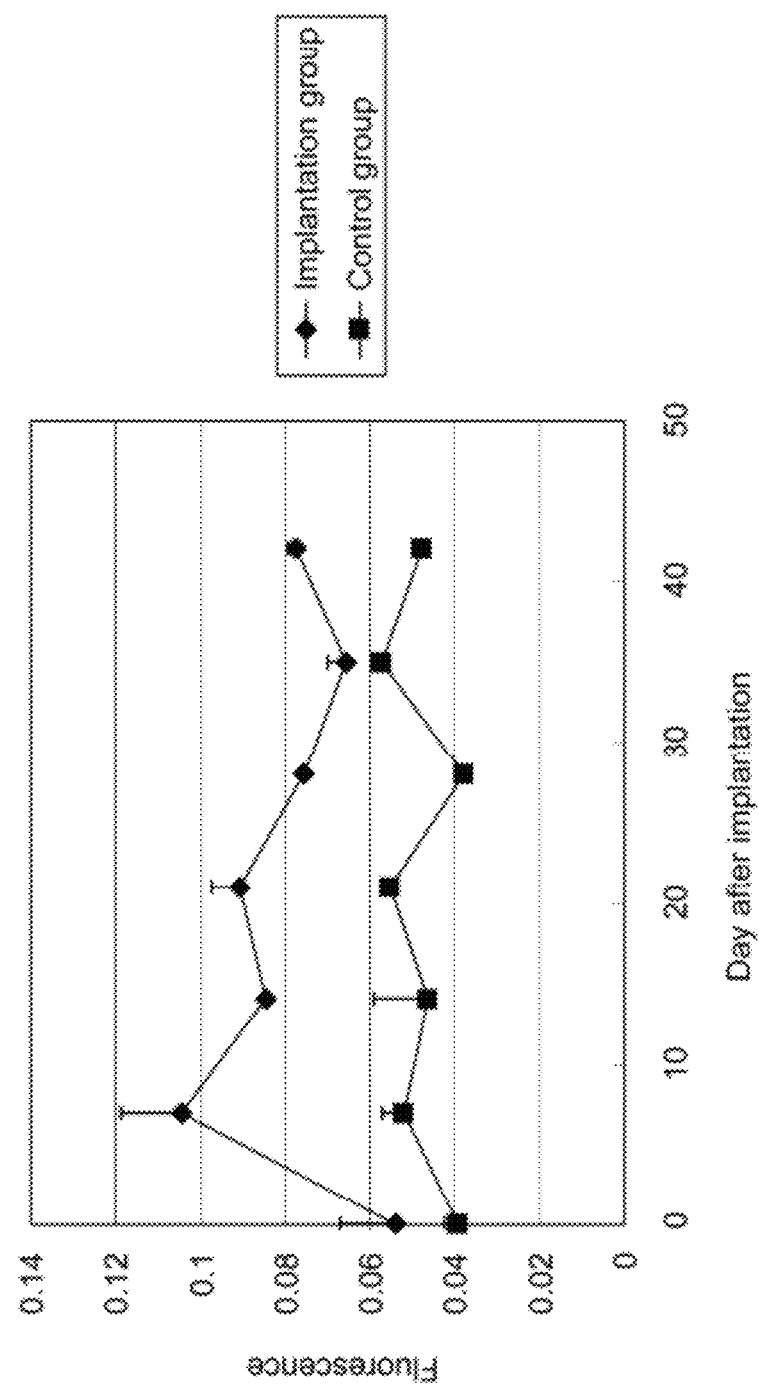
FIG. 20 is a graph showing the results of collecting the hydatoid of a rabbit after PEG capsule implantation to measure fluorescence intensity.
Figure 21:
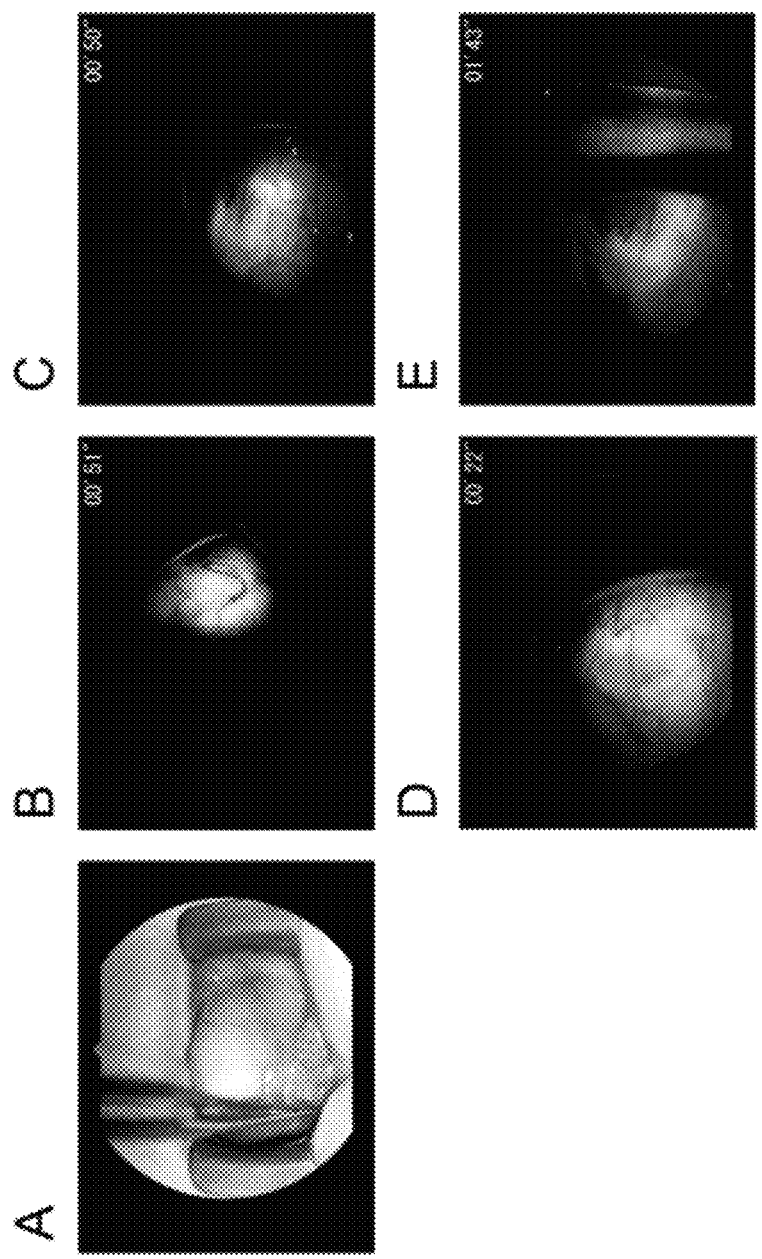
FIG. 21 is a series of photographs of the fluorescence distribution in the periphery of an implanted PEG capsule, taken using a fluorescence fundus camera.

In the DDS of the present invention, drugs used for the treatment of diseases such as the above eye disease include a drug suppressing vascularization, a drug promoting the growth of nerve cells, a drug protecting nerve cells, a steroid drug, a therapeutic drug for glaucoma, an anti-inflammatory drug, an antifungal drug, and an anticancer drug. In addition, examples of the vascularization-suppressing drug include vasohibin; examples of the drug promoting the growth of nerve cells include BDNF (Brain-derived neurotrophic factor); and examples of the steroid drug include betamethazone and hydrocortisone. Examples of the therapeutic drug for glaucoma include prostaglandin-related drugs (latanoprost, travoprost, tafluprost, unoprostone, etc.), sympatholytic drugs (timolol maleate, gel-forming timolol, carteolol hydrochloride, betaxolol hydrochloride, levobunolol hydrochloride, nipradilol, bunazosin hydrochloride, etc.), and carbonate dehydratase inhibitors (dorzolamide hydrochloride, brinzolamide, etc.), which are drugs focused on lowering intraocular pressure The drug-containing PEG capsule as the DDS of the present invention is inserted into the body as an implant. The insertion is preferably carried out near an affected part. For example, for a DDS for treating eye disease, it is inserted as an implant into the sclera. As used herein, the sclera refers to a portion from above the choroid to under the conjunctiva, that is, the subsclera, the inside of the sclera, the episclera, the subconjunctiva, and the suprachoroid. The DDS requires no vitreous surgery for implantation and can be safely and simply implanted. Thus, the DDS of the present invention is a non-invasive. Specifically, the PEG capsule may be implanted the sclera outside the eye (FIG. 3). On this occasion, it is implanted so that the cap part consisting of a porous PEG sheet from which a drug is released contacts the side of the eyeball. A means for fixing the PEG capsule in the body may be provided in the PEG capsule. The fixation may be performed in a state of contact with the body using a thread such as a surgical suture, and a hole or a concave or convex portion for tying the thread may be provided in the PEG capsule. Such a PEG capsule is illustrated in FIG. 18. The PEG capsule illustrated in FIG. 18A has a hole for suture for fixation to the sclera, and a thread can be passed therethrough and sutured to the sclera to fix the capsule. The PEG capsule illustrated in FIG. 18B has concave portions resulting from the removal of the corners of the capsule, and the concave portions can be crosswise tied using a thread for fixation. Such implantation causes the drug released from the pores of the porous PEG sheet to reach the inside of the eye through the sclera without dispersion to other parts. FIG. 19 shows the appearance of implantation to the sclera of rabbit's eye. FIG. 20 shows the results of measuring the transfer of a drug into the eye based on fluorochrome intensity in the hydatoid. The implanted eye had significantly higher fluorescence intensity in a sustained manner for 1 month or more, showing that the drug transferred into the eye in a sustained manner. Even after 1 month, the fluorochrome sufficiently remains in the device on the sclera, showing that sustained slow release is possible for several months or more (FIG. 21). Thus, the DDS of the present invention is a transscleral DDS.

A drug is slowly released from the capsule for a long period of time, enabling the drug to be locally administered in a sustained manner to an affected part. In addition, the PEG capsule of the present invention is easily removed; it can be detached without any surgery when treatment has become unnecessary or when side effects have occurred. Thus, the DDS of the present invention is a detachable DDS.

The dosage and dosing period of a drug can be controlled by the amount of the drug contained in the PEG capsule, the amount and degree of cross-linking of collagen forming the collagen particles or the collagen gel, the amount and degree of cross-linking of PEG forming the PEG pellet, the porosity of the porous PEG sheet, the molecular weight of PEGDM in the porous PEG sheet, the shape of the PEG capsule, and the like. Particularly, the porosity of the porous PEG sheet can be regulated to control the substance permeability from the porous PEG sheet to control the dosage and dosing period thereof. The dosage and dosing period may also been properly set depending on the type and severity of eye disease.

For example, the DDS of the present invention is used to administer 0.01 to 100 mg of a drug over at least 1 month, preferably at least 3 months, more preferably at least 6 months, more preferably at least 1 year, more preferably at least 2 years, more preferably at least 3 years, more preferably at least 4 years, more preferably at least 5 years.

The present invention encompasses a method for treating a disease such as eye disease by administering a therapeutic drug to patients by the slow release of the drug in the body using the drug slow-releasing implant and the sustained drug delivery system in which the implant is implanted in the body according to the invention.

The present invention is described below in detail, based on Examples. However, the invention is not intended to be limited by these Examples.

1. Preparation of Collagen Particle Impregnated with FITC-Dextran 40 kDa (FD40)

The following operations were all carried out at room temperature. In a 100-ml beaker was placed 10 ml of a 1% collagen aqueous solution (derived from the pig hide, Nippon Meat Packers, Inc.). Thereto was added 50 ml of liquid paraffin (WAKO), which was then stirred at 600 rpm for 5 minutes using a stirrer (High Power Mixer, P-2, AS ONE Corporation). Thereto was added 3 ml of Span 20 in liquid paraffin, which was further stirred at 600 rpm for 5 minutes. Thereto was added 1 ml of a 20 mg/ml FD40 aqueous solution, which was then stirred at 600 rpm for 5 minutes. Thereto was added 1 ml of a 1% water-soluble carbodiimide (WAKO, WSC) aqueous solution, which was then stirred at 600 rpm for 60 minutes. Thereto was added 50 ml of 50% ethanol (WAKO), which was then stirred at 600 rpm for 5 minutes. The mixture was centrifuged at 3,500 rpm for 5 minutes. The supernatant was discarded, and 30 ml of fresh 50% ethanol was added thereto and vortexed for 30 seconds. The operations of the centrifugation and 50% ethanol addition were repeated twice. To a collagen particle (Coll particle) pellet after centrifugation was added 30 ml of phosphate buffered saline (PBS), which was vortexed for 30 seconds. The mixture was centrifuged at 3,500 rpm for 5 minutes. The supernatant was discarded, and 30 ml of fresh PBS was added thereto and vortexed for 30 seconds. The mixture was centrifuged at 3,500 rpm for 5 minutes. The operations of the centrifugation and PBS addition were repeated twice. The pellet after centrifugation was used as Coll particles impregnated with FD40 (Coll-FD40) for the following operations. The average particle diameter of Coll-FD40 was 8.7 μm (FIG. 4). Coll particles for the preparation of a porous poly(ethyleneglycol) dimethacrylate (PEGDM) sheet to be described below used those not impregnated with FD-40. This was carried out by all the same methods except for omitting the operation of adding the 20 mg/ml FD40 aqueous solution in the above operation. The average diameter of the Coll particles was the same 8 to 10 μm as that of Coll-FD40.

2. Preparation of PEGDM Pellet Including Coll-FD40

A PEGDM/Coll-FD40 pellet in which the above Coll-FD40 was embedded in PEGDM (Mn=875, Aldrich) was prepared. A PEGDM aqueous solution of 1 mg/ml PEGDM and 10 μg/ml 2-hydroxy-2-methyl-propiophenone was first prepared. The PEGDM aqueous solution and Coll-FD40 were then mixed at a volume ratio of 1:1. The mixture was cast into a mold and irradiated with UV light to cure PEGDM to provide a pellet (PEGDM/Coll-FD40).

3. Preparation of Porous PEGDM Sheet

Figure 5:
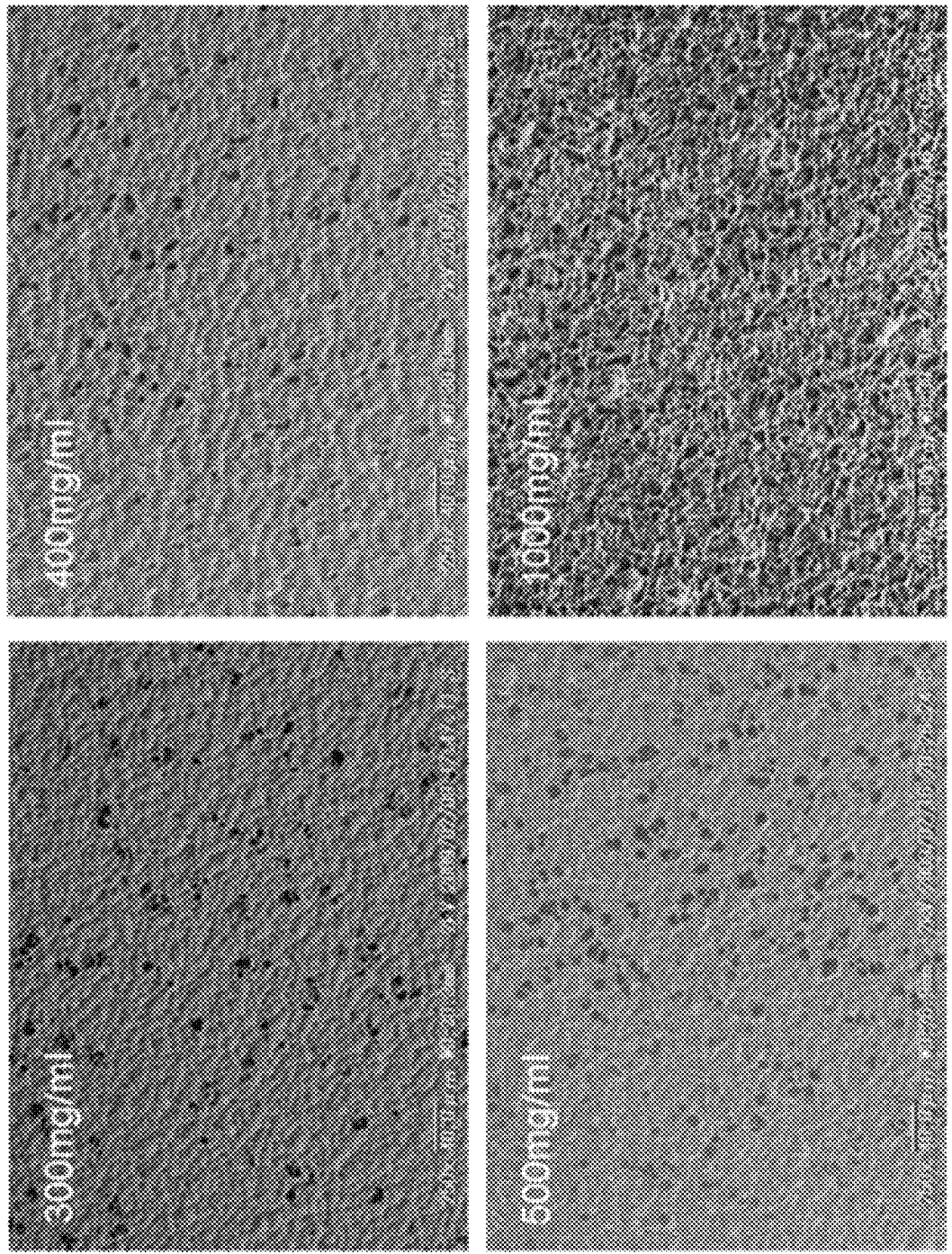
FIG. 5 is a series of photographs showing electron micrograms of porous PEG sheets.
Figure 6:
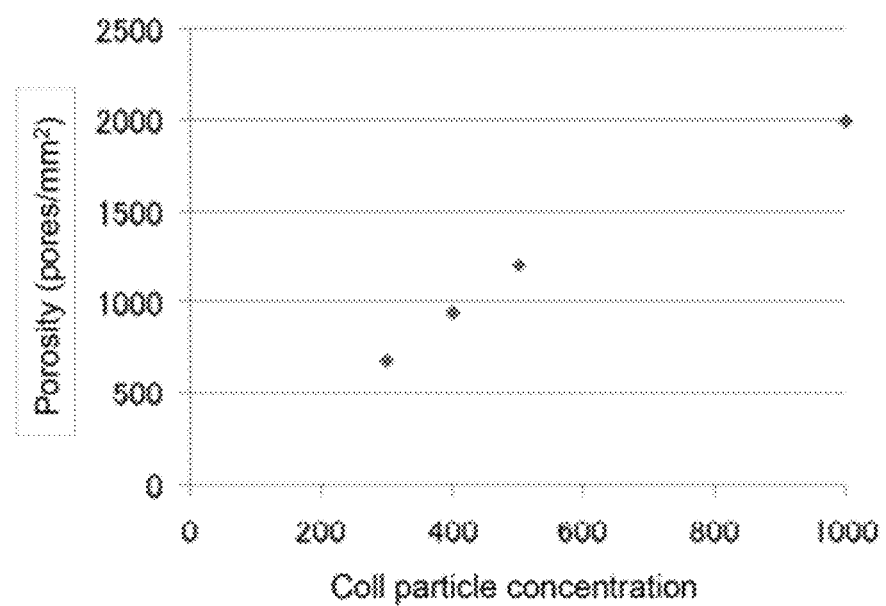
FIG. 6 is a graph showing a relationship between the concentration of Coll particles when a porous PEG sheet is prepared and the porosity of the resultant porous PEG sheet.

A porous PEGDM sheet was prepared using Coll particles as a porogen (a mold for making porous). A NC machine tool was first used to prepare a mold for thin membrane making, having an inside dimension of 50 mm×50 mm×0.3 mm. Coll particles were mixed in concentrations of 100, 200, 300, 400, 500, and 1,000 mg/ml in a PEGDM aqueous solution of 1 mg/ml PEGDM and 10 μg/ml 2-hydroxy-2-methyl-propiophenone. Each mixture was poured into the mold for thin membrane making, the top of which was then capped with a slide glass and irradiated with UV light (11.85 mW/cm$^2$) for 90 seconds to cure PEGDM. Thereafter, the resultant was extracted from the mold to provide a PEGDM thin membrane. In addition, the PEGDM thin membrane was immersed in 50 U/ml collagenase in PBS for 48 hours to enzymatically degrade Coll particles to provide a porous PEGDM sheet. An electron photomicrograph of each concentration of Coll particles is shown in FIG. 5. Coll particle portions are shown to have become pores. As a result of measuring porosity from the photographs, the amount of Coll particles and the porosity are found to be correlative with each other (FIG. 6).

4. Substance Permeability of Porous PEGDM Sheet

Because most drugs are of 40 kDa or less (steroid: 0.3 kDa, BDNF: 27 kDa, VEGF: 38 kDA, Vasohibin: 32 kDa), FD40 was used as a model drug to evaluate the substance permeability of a porous PEGDM sheet. The membrane attached to the bottom of a cell culture insert (Intercell TP, hereinafter sometimes referred to as "insert", Kurabo Industries Ltd.) was peeled, and the porous PEGDM sheet prepared by the above-described method was pasted with an adhesive (Aron alpha). The insert was disposed on a 24-well cell culture plate (Greiner), and 0.1 ml of a 5 mg/ml FD40 aqueous solution was placed in the insert. In addition, 0.4 ml of PBS was placed in the underneath well, followed by incubation at 37° C.

Figure 7:
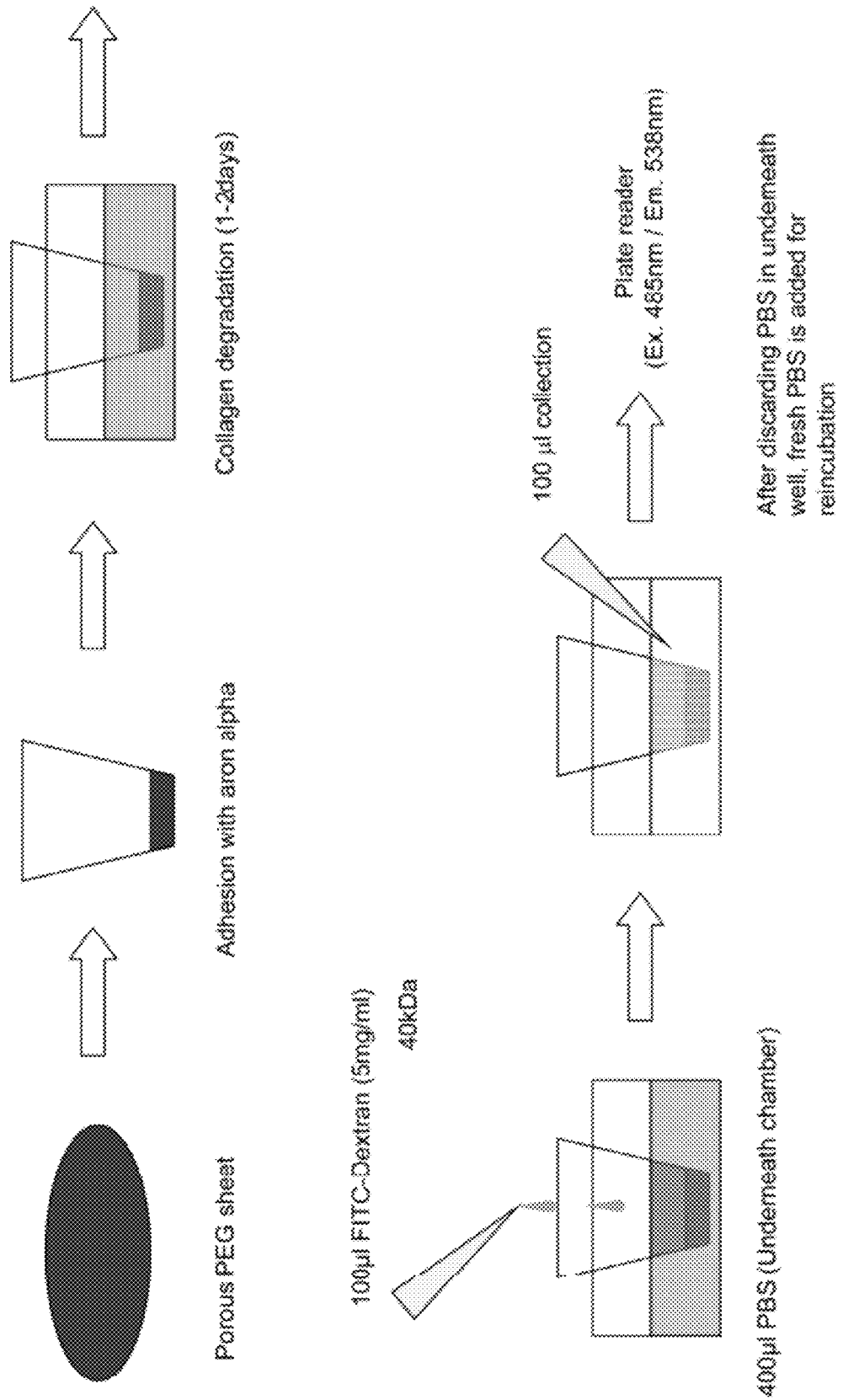
FIG. 7 is a flow diagram summarizing a method for evaluating the substance permeability of a porous PEG sheet.
Figure 8:
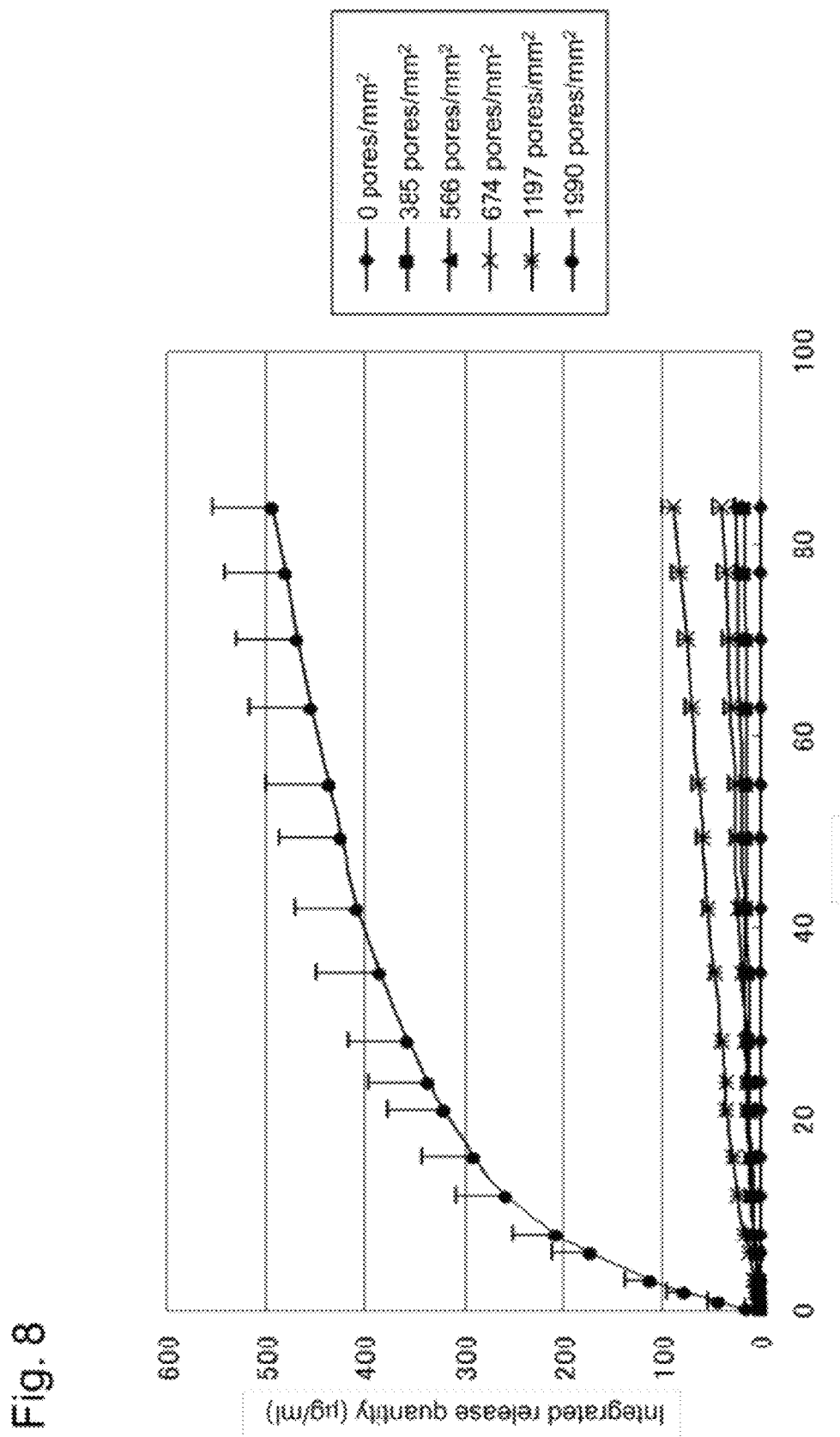
FIG. 8 is a graph showing a relationship between the porosity and the substance permeability of a porous PEG sheet.

The amount of FD40 having passed through the porous PEGDM sheet was estimated by measuring the fluorescence intensity of PBS in the underneath well. The outline of a method for evaluating the substance permeability of the porous PEGDM sheet is shown in FIG. 7. After incubation for a predetermined time, 0.1 ml of PBS was sampled from the underneath well and transferred to a black 96-well multiplate (Sumiron). FD40 in PBS was measured using a fluorescence plate reader (Ascent, Fluoroscan, ex. 485 nm/em. 538 nm). After sampling, PBS in the underneath well was removed by aspiration, and 0.4 ml of fresh PBS was added thereto, which was then reincubated. During incubation, the edge of the plate was sealed with a vinyl tape without producing any clearance to prevent the evaporation of PBS and FD40 in the well. The fluorescence-measured value of the sample was converted to the concentration (μg/ml) of FD40 from a calibration curve of FD40 (obtained by measuring the fluorescence intensity of a ½ dilution series of a 1,000 μg/ml FD40 aqueous solution) prepared in advance. The graph was shown using integrated values of FD40 (cumulative release). A graph on slow release is in FIG. 8. The FD40 permeability varied in a manner dependent on the concentration (porosity) of Coll particles. This indicates that the concentration of Coll particles can be changed to control the substance permeability (slow releasing capability) through the porous PEGDM sheet. The initial burst was suppressed for a porous PEGDM sheet having a porosity of 500 mg/ml (1,197 pores/mm$^2$) or less.

5. FD40 Slow Releasing Capability of Coll-FD40 and PEGDM/Coll-FD40

Figure 9:
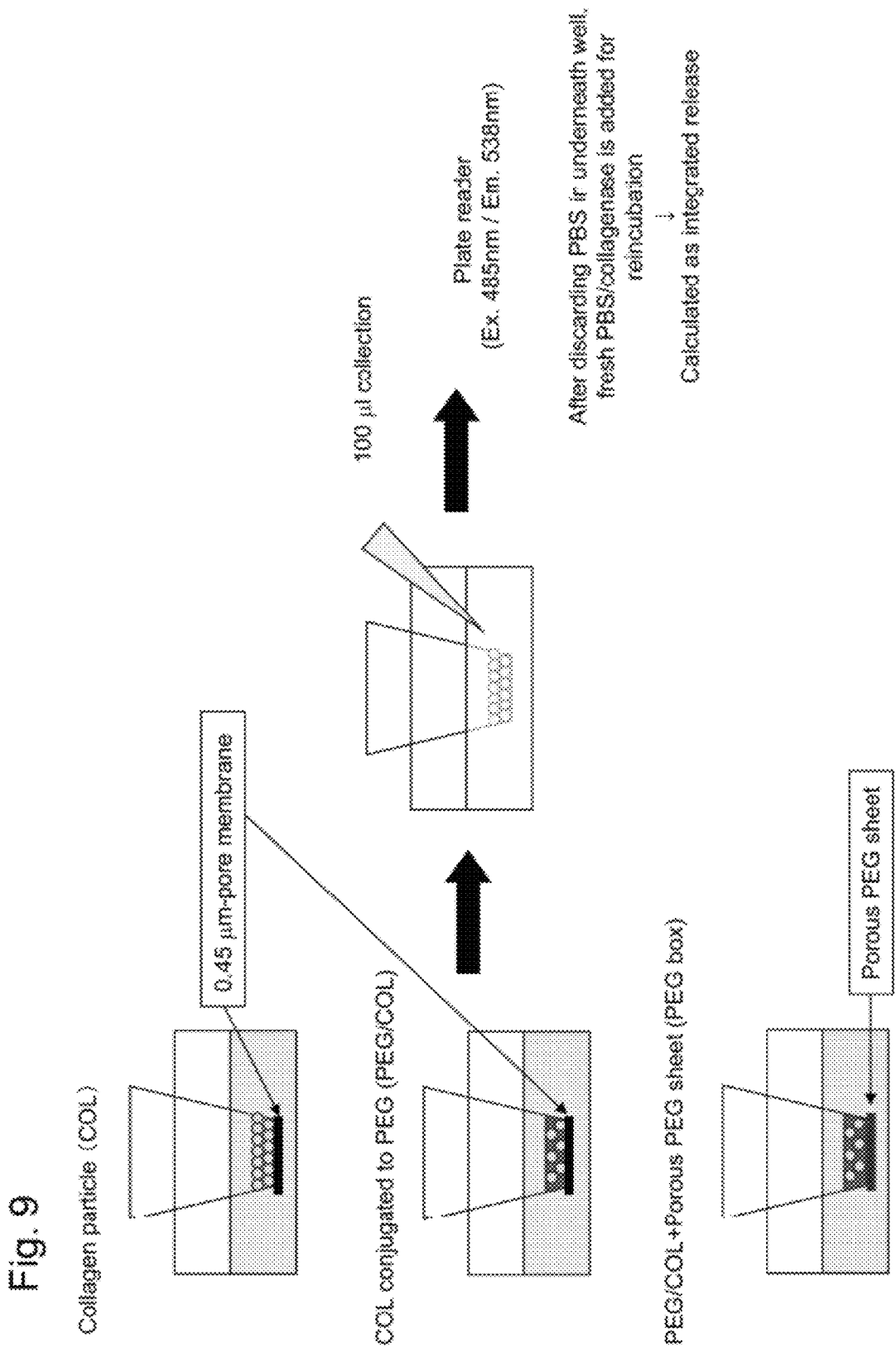
FIG. 9 is a flow diagram summarizing a method for evaluating slow-releasing capability.
Figure 10:
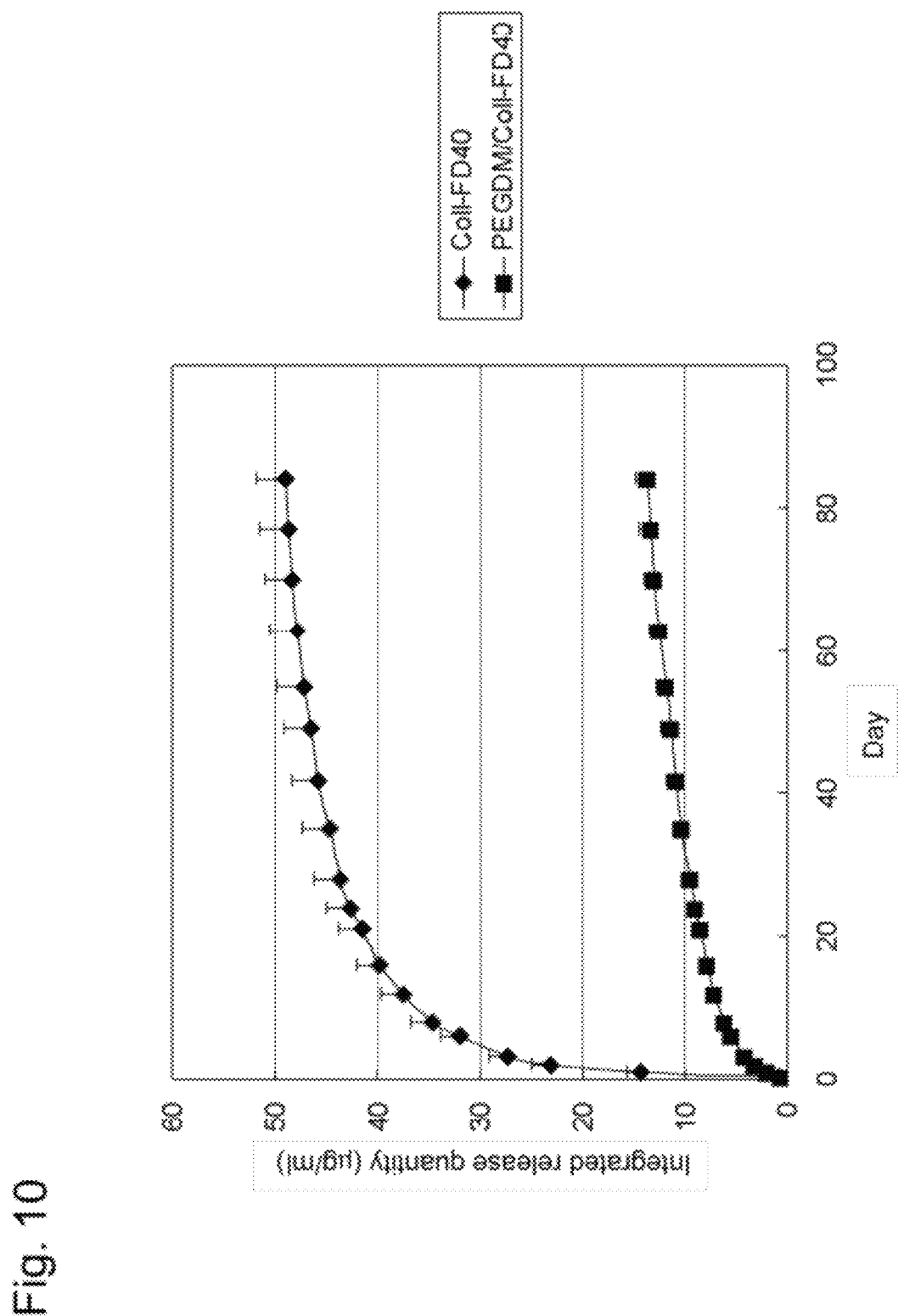
FIG. 10 is a graph showing the slow-releasing capabilities of Coll-FD40 (Coll particles impregnated with FITC-Dextran 40 kDa) and PEGDM/Coll-FD40 (PEG pellet containing Coll particles impregnated with FITC-Dextran 40 kDa).

The FD40 slow release from Coll-FD40 and PEGDM/Coll-FD40 was evaluated. A 5 mg/ml FD40 solution (100 μl), Coll-FD40 (100 mg, and PEGDM/Coll-FD40 (100 mg) each placed in an untreated cell culture insert were provided. Coll-FD40 was used after dilution by 2-fold with water so that its amount is equivalent to that of Coll-FD40 in PEGDM/Coll-FD40. The pore of the insert is of 0.45 μm, indicating no influence on the FD40 permeability. These inserts were disposed on a 24-well cell culture plate (Greiner), and 0.4 ml of PBS was placed in the underneath well, followed by incubation at 37° C. After a predetermined time, PBS was sampled from the underneath well, and fluorescence intensity was measured as described above to estimate the FD40 amount. The outline of a method for evaluating slow-releasing capability is shown in FIG. 9. A graph on slow release is in FIG. 10. The FD40 solution is not described in the graph because it completely passed therethrough immediately after the start of testing. The impregnation of FD40 in Coll particles was shown to result in long-term suppressed slow-releasing capability. In addition, it was shown that Coll particles could be pelletized together with PEGDM to control the speed of slow release.

6. FD40 Slow-Releasing Capability of Coll-FD40 and PEGDM/Coll-FD40 through Porous PEGDM Sheet Assuming the insert having the porous PEGDM sheet attached as the PEGDM capsule, the slow release of FD40 from the insert was evaluated. Coll-FD40 and PEGDM/Coll-FD40 were each placed in the insert and compared for slow-releasing capability.

Figure 11:
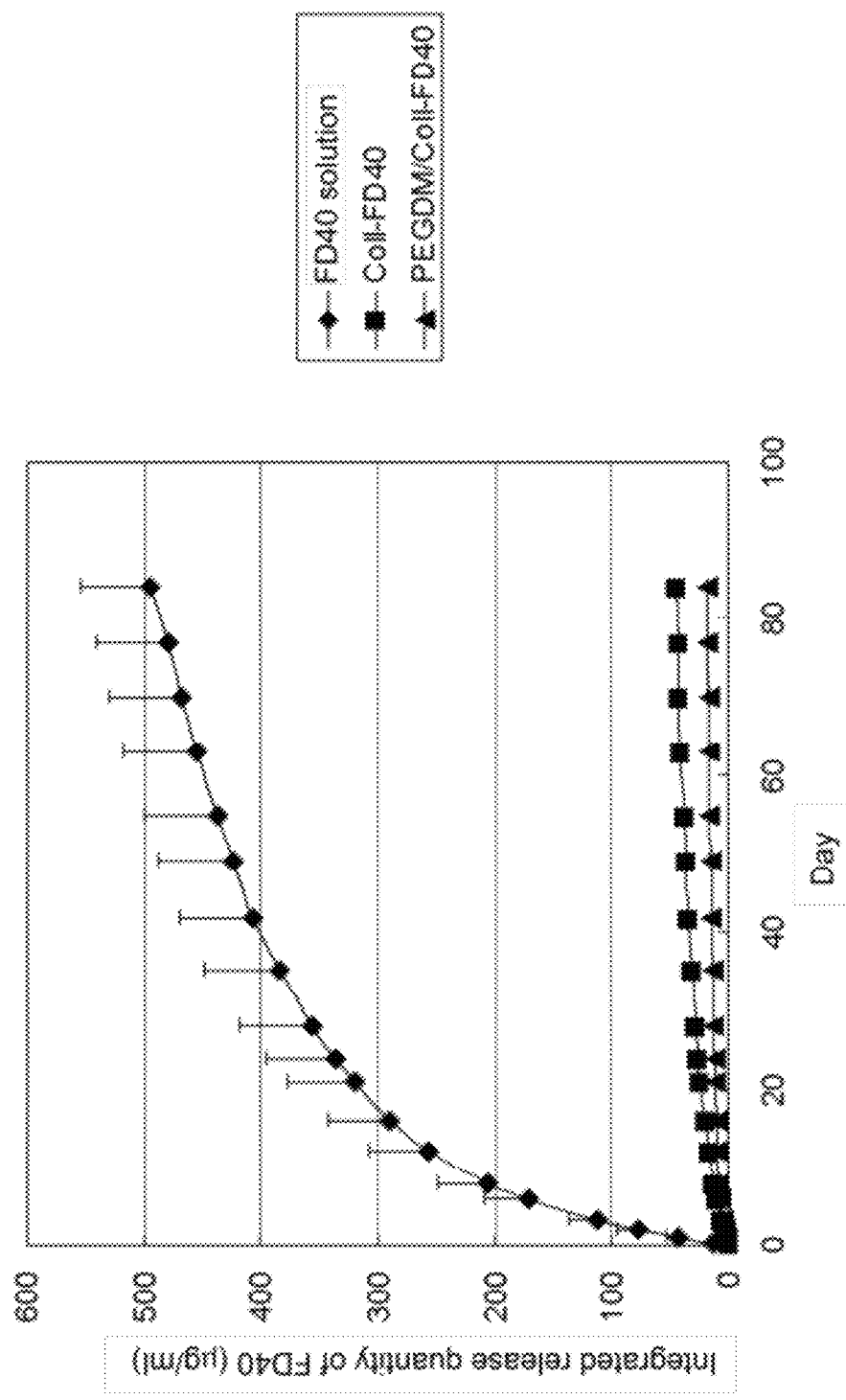
FIG. 11 is a graph showing the difference in slow release capability due to the difference in the form among the slow release carriers of FD40 solution, Coll-FD40 (Coll particles impregnated with FITC-Dextran 40 kDa), and PEGDM/Coll-FD40 (PEG pellet containing Coll particles impregnated with FITC-Dextran 40 kDa).

Coll-FD40 (100 mg) and a PEGDM/Coll-FD40 pellet (100 μl) placed in the above insert having the porous PEGDM sheet (1,000 mg/ml) attached were provided. Here, Coll-FD40 was used after dilution by 2-fold with water so that its amount is equivalent to that of Coll-FD40 in PEGDM/Coll-FD40. These inserts were disposed on a 24-well cell culture plate (Greiner), and 0.4 ml of PBS was placed in the underneath well, followed by incubation at 37° C. After a predetermined time, PBS was sampled from the underneath well, and fluorescence intensity was measured as described above to estimate the FD40 amount. A graph on slow release is shown in FIG. 11. FIG. 11 showed that the impregnation of FD40 in Coll particles could suppress the speed of slow release to about 1/10. In addition, it was shown that the pelletization of Coll particles with PEGDM could further suppress the speed of slow release to about 1/2. From the above-described results, it was demonstrated that the PEGDM/Coll-FD40 pellet showed the suppressed initial burst and linear slow-releasing characteristics for a long period of time. The results show that the form of a carrier packed in the capsule can be changed (a solution, particles, or a PEGDM pellet) to control slow-releasing characteristics.

Coll-FD40 and a PEGDM/Coll-FD40 pellet were considered as a 1 step slow release DDS in the present invention; the results of comparing the slow release of a drug from the DDS with that from the PEGDM/Coll-FD40 through the porous PEGDM sheet as a 2 step slow release DDS (porous PEGDM sheet; 0, 100, 500 mg/ml) are shown in FIG. 12. FIG. 12 showed that the combination of the PEGDM pelletization and the porous PEGDM sheet could achieve linear slow release in which the initial burst was suppressed over a long period of time (as estimates, 5.43 years: 100 mg/ml, 1.98 years: 500 mg/ml).

7. Preparation of PEGDM Capsule Having Porous PEGDM Sheet

Figures 1, 13B:
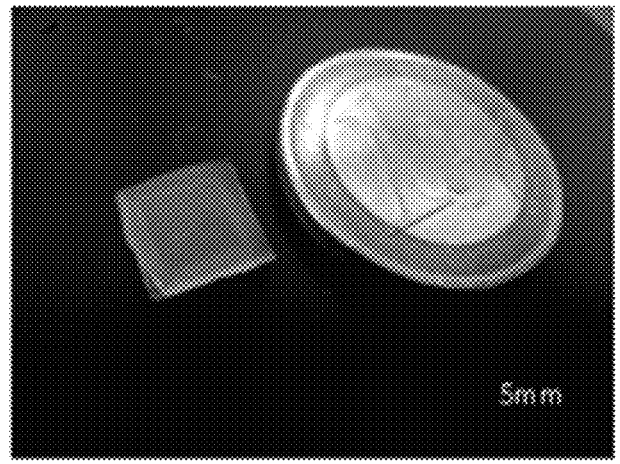
Figures 2, 13B:
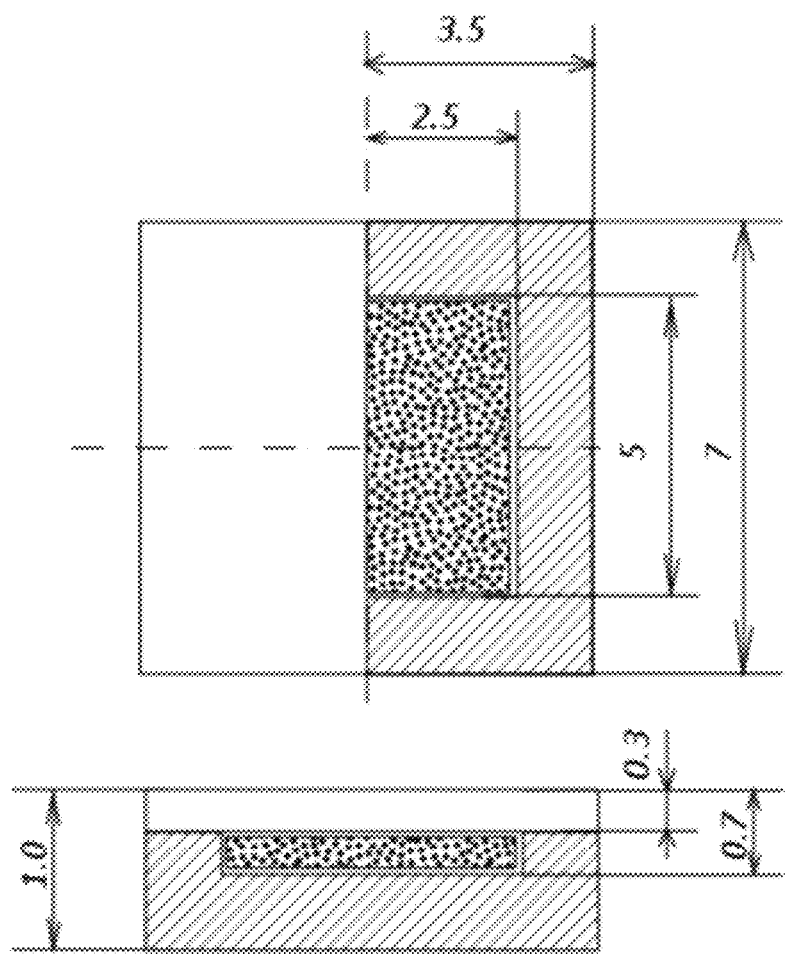
Figure 14A:
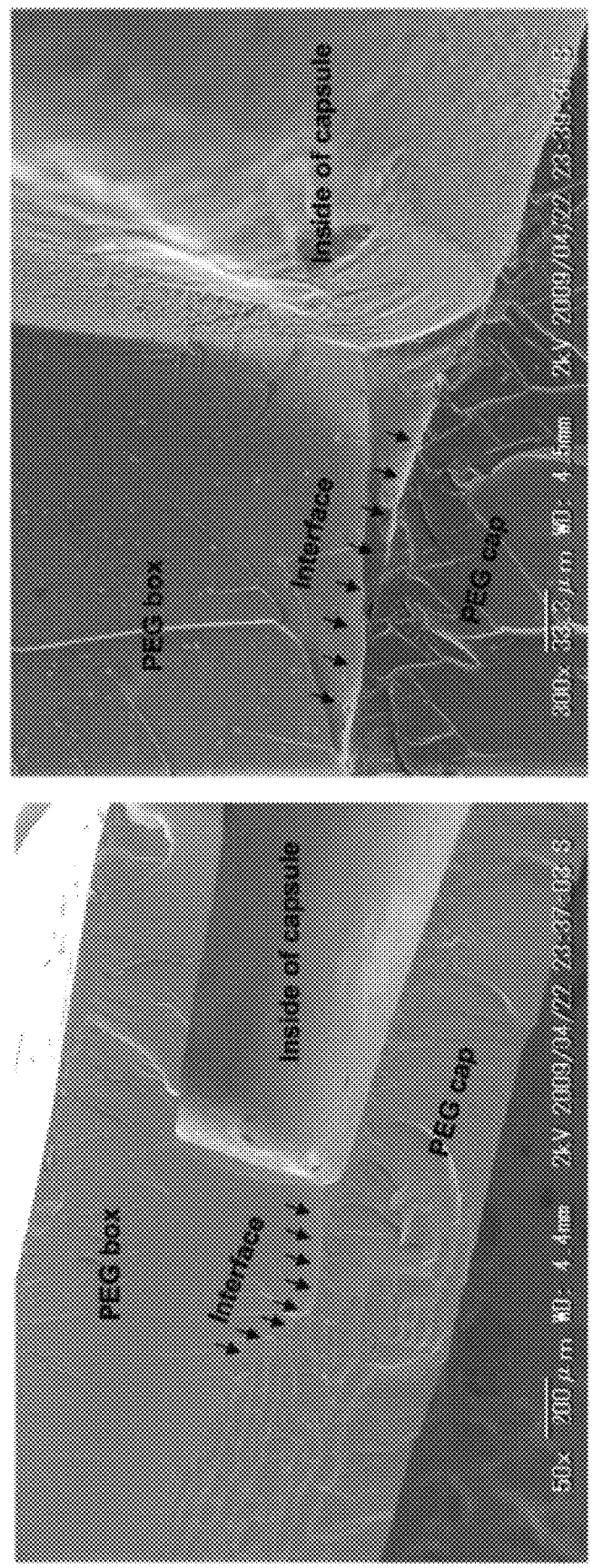
FIG. 14A is a pair of photographs each showing a microscopic appearance of the interface of a PEG box and a porous PEG sheet (PEG cap).
Figure 14B:
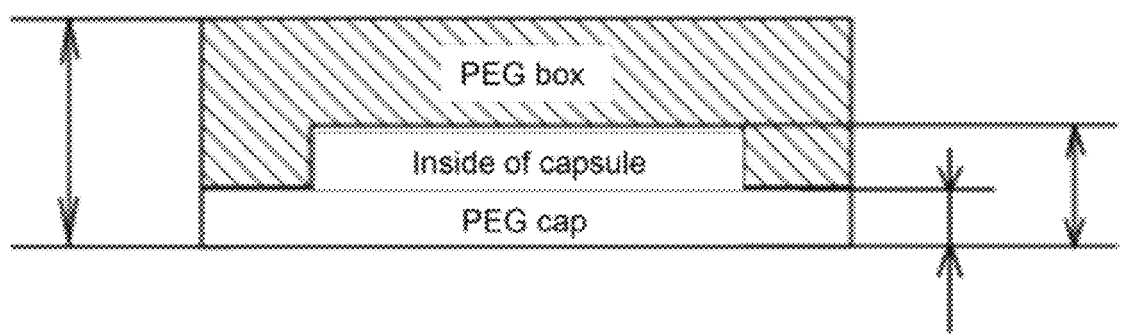
FIG. 14B is a schematic diagram showing the interface of a PEG box and a porous PEG sheet (PEG cap).

As in preparing a mold for thin membrane making, a mold comprising boxes (the inside dimension of 1 well: 5.0 mm×5.0 mm×0.4 mm) disposed in a reticular pattern was prepared using an NC machine tool (FIGS. 13A-1 and 13A-2). A PEGDM aqueous solution of 1 mg/ml PEGDM and 10 μg/ml 2-hydroxy-2-methyl-propiophenone was cast into the mold. The mold was capped with a slide glass, and irradiated with UV light (11.85 mW/cm$^2$) for 2 minutes to cure PEGDM. Thereafter, the resultant was extracted from the mold to provide a PEGDM box. PEGDM/Coll-FD40 was disposed in the PEGDM box, which was then capped with the above porous PEGDM sheet (500 mg/ml) and irradiated with UV light to adhere the porous PEGDM sheet to the PEGDM box. Then, any number of the arrayed wells were cut off to prepare PEGDM capsules (FIG. 13A-1 and 13A-2 and B). FIGS. 13A-1 and 13A-2 are drawings of arrayed PEG boxes, and FIGS. 13B-1 and 13B-2 are drawings of single PEG boxes. From the electron microscope images of FIGS. 14A and 14B, it was confirmed that the cap and the box were joined without any clearance.

Figure 15A:
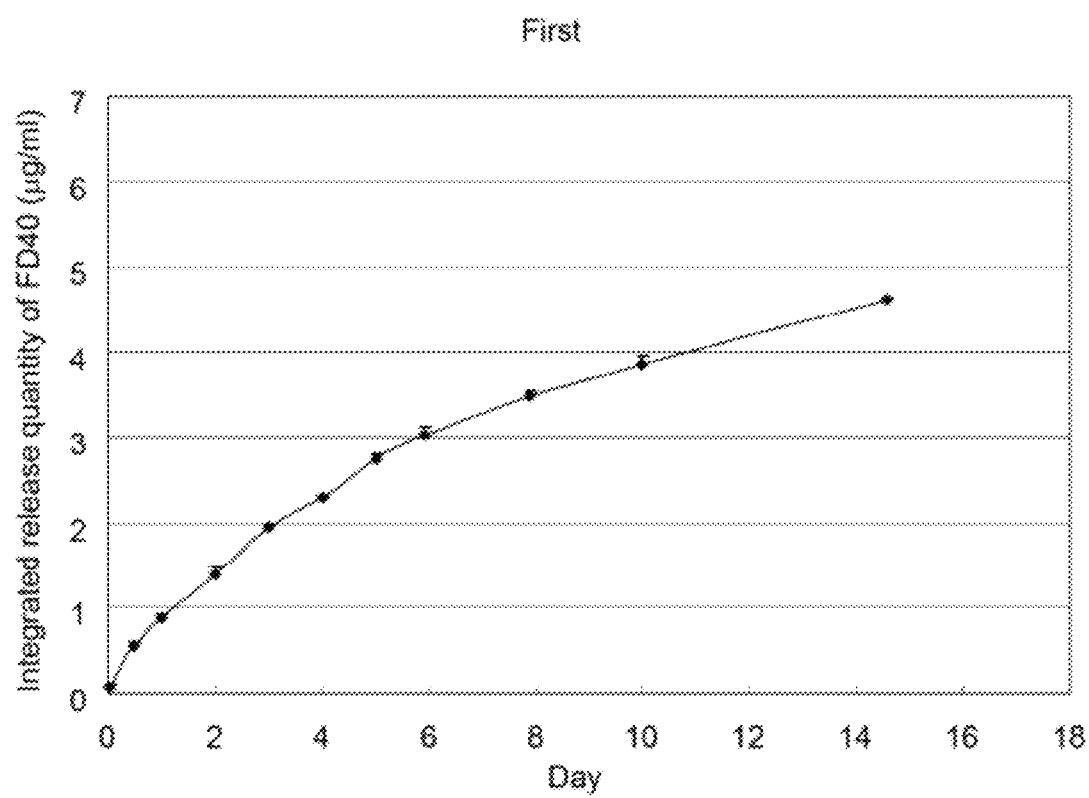
FIG. 15A is a graph showing slow release from PEGDM/Coll-FD40 (PEGDM pellet containing Coll particles impregnated with FITC-Dextran 40 kDa) packed in a PEG box (first).
Figure 15B:
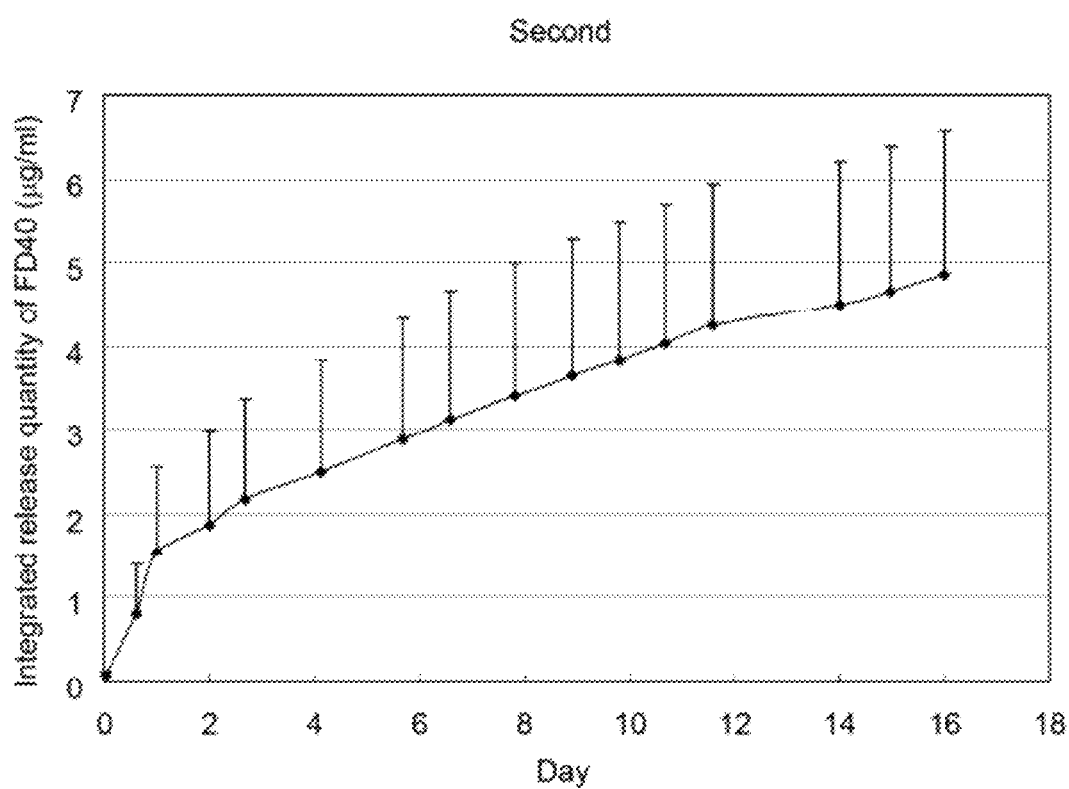
FIG. 15B is a graph showing slow release from PEGDM/Coll-FD40 (PEGDM pellet containing Coll particles impregnated with FITC-Dextran 40 kDa) packed in a PEG box (second).

In addition, the FD40 slow-releasing characteristics of the prepared PEGDM box-shaped capsule were determined. The prepared PEGDM capsule was disposed in a dish, to which 1 ml of PBS was placed, followed by allowing to stand at 37° C. PBS sampled from the dish at each time was measured using a fluorescence plate reader (Ascent, Fluoroscan, ex. 485 nm/em. 538 nm) to evaluate the slow-releasing characteristics of the PEGDM capsule. The results in duplicate are shown in FIGS. 15A and B. Both results showed almost the same slow release amount and slow releasing characteristics as those in the results of the cell culture insert test (PEGDM/Coll-FD40+ porous PEGDM sheet (500 mg/ml) in FIG. 12), indicating that the PEGDM capsule could function. Change to Coll-FD40 or FD40 in the capsule is also predicted to result in the same slow-releasing characteristics as in FIGS. 11 and 12.

Figure 23:
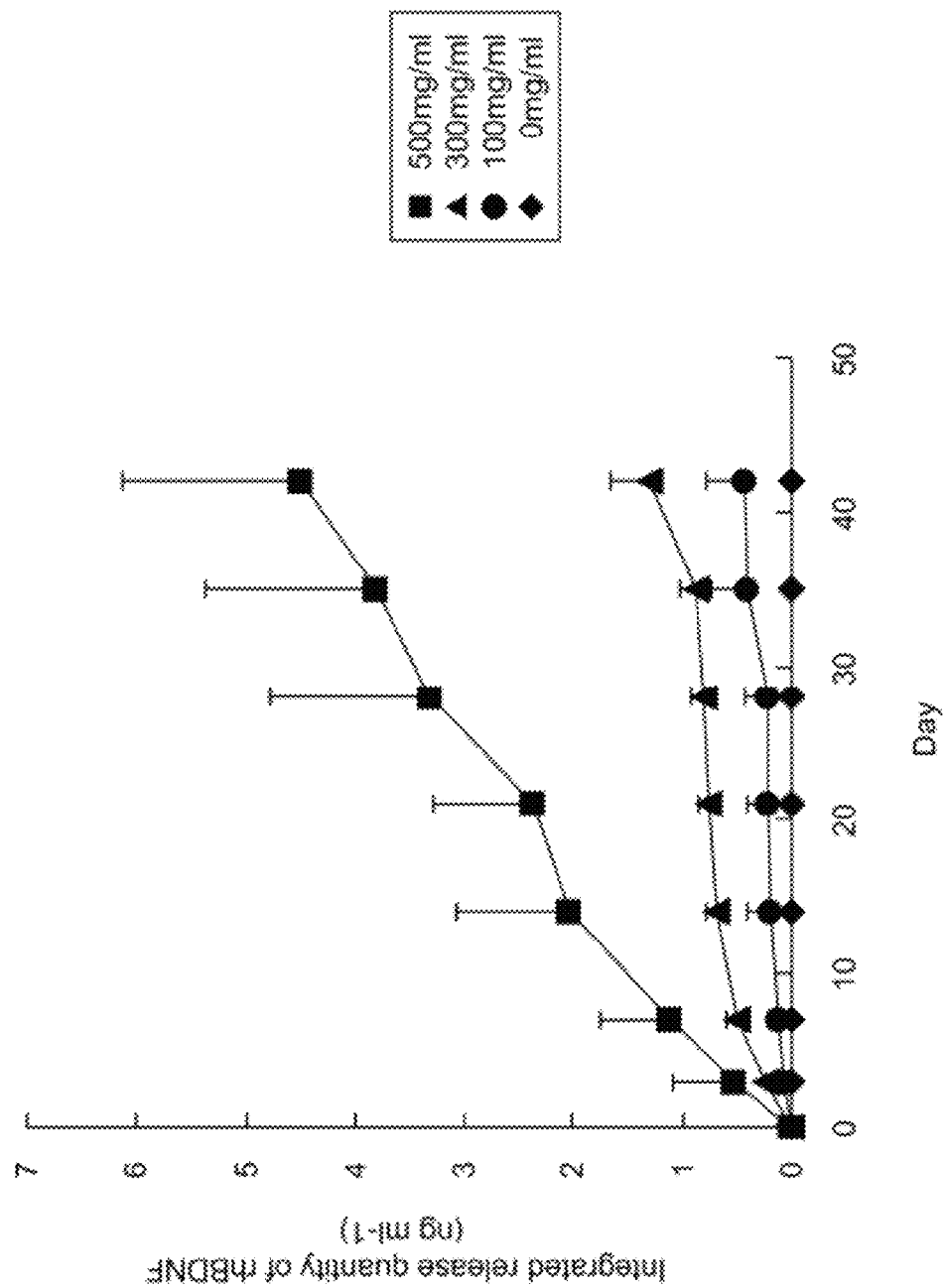
FIG. 23 is a graph showing the slow release of BDNF from a PEG capsule containing BDNF.

The slow release from a capsule packed with BDNF was also measured. Human recombinant BDNF (rhBDNF, Wako Pure Chemical Industries Ltd.) was impregnated in collagen particles to 20 μg/ml, and capsulated using a porous PEG sheet in which 0, 100, 300, or 500 mg/ml of collagen particles was mixed; the slow-releasing characteristics here are shown in FIG. 23. It was shown that the slow-releasing capability could be controlled in a manner dependent on the concentration of collagen particles in the porous PEG sheet. The capsule was shown to exhibit zero order slow release without the initial burst over 6 weeks.

8. Low Molecular Weight Drug Slow-Releasing Capability of Porous PEGDM Sheet when Molecular Weight of PEGDM is Changed Sheets having changed mixing ratios of PEGDM (Mn 750) and TEGDM (Mw 286.3) were prepared to evaluate their low molecular weight drug slow-releasing capability. The low molecular weight drug used sodium fluorescein (FA, a fluorescent contrast agent clinically used) as a model. PEG sheets were prepared in the 6 patterns of PEGDM:TEGDM=100:0, 95:5, 90:10, 80:20, 50:50, and 0:100; FA was capsulated; and the capsules were immersed in PBS to measure the fluorescence intensity at regular intervals. The results are shown in FIG. 16. The increased mixing ratio of TEGDM suppressed the FA slow-releasing capability. The slow-releasing capability was irrespective of the presence of collagen particles. Thus, lower molecular weight PEGDM was shown to be effective in controlling the slow release of a low molecular weight drug.

9. Implantation to Rabbit's Eye

Figure 22:
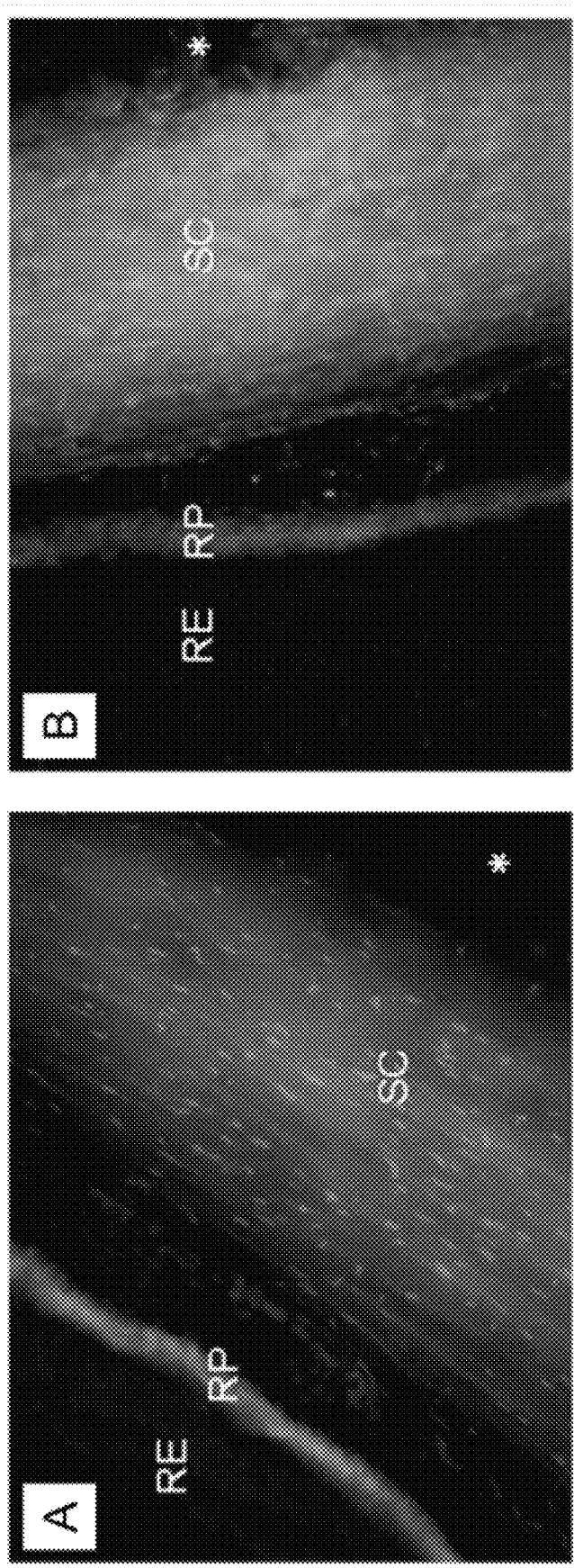
FIG. 22 is a pair of tissue photographs in the periphery of the retina of rabbit's eye 3 days after the implantation of PEG capsules containing fluorescein and FD40.

A capsule (the collagen particle concentration of its porous PEG sheet: 500 mg/ml) packed with a PEG pellet of FA was implanted on the sclera of the eye of rabbits. One eye of each rabbit was used as a non-implantation control. The conjunctiva was incised 5 mm and the capsule was implanted therethrough into 2 to 15 mm of the corneal limbus. The capsule was fixed by suture. The conjunctiva was finally sutured to terminate the implantation. The hydatoid (100 μl) was collected every other week and the fluorescence intensity thereof was measured using a fluorescence plate reader. Using a fluorescence camera, the fluorochrome in the device implanted on the sclera and the distribution of the pigment slowly released were photographed. As a result, the capsule-implanted group showed a significantly higher fluorescence intensity of the hydatoid over 1 month or more (FIG. 20). These data suggest the transfer of the drug into the eye because it is probable that the drug transferred to the vitreous body in the eye and some of the drug transferred to the anterior chamber. The fluorescence camera confirmed the presence of fluorescence inside and around the device, suggesting that the drug was slowly released locally and sustainably in the implanted site (FIG. 21). In addition, as a result of evaluating tissue 3 days after implantation, strong fluorescence was observed in the sclera (SC) and the subretina (RP) for both FA and FD40, showing that the drug had reached the retina (FIG. 22). In FIG. 22, the fluorescences of the cell nucleus (blue fluorescence) and the model drug (green fluorescence) are observed. In FIG. 22, the mark * represents the position in which the PEG capsule was present. The white belt-like portion in the vicinity of RP (retinal pigment epithelium) and SC (sclera) shows the green fluorescence of the model drug (FA), and the white point-like portion of RE (retina) and between RP and SC shows the blue fluorescence of the cell nucleus (DAPI). FIG. 22 shows that the model drug passes through RP. When the drug passes through RP, the drug is fed to RE. Because RP has a high barrier function, the pigment stops here and is concentrated.

10. Structural Evaluation of Implanted Capsule

Figure 24:
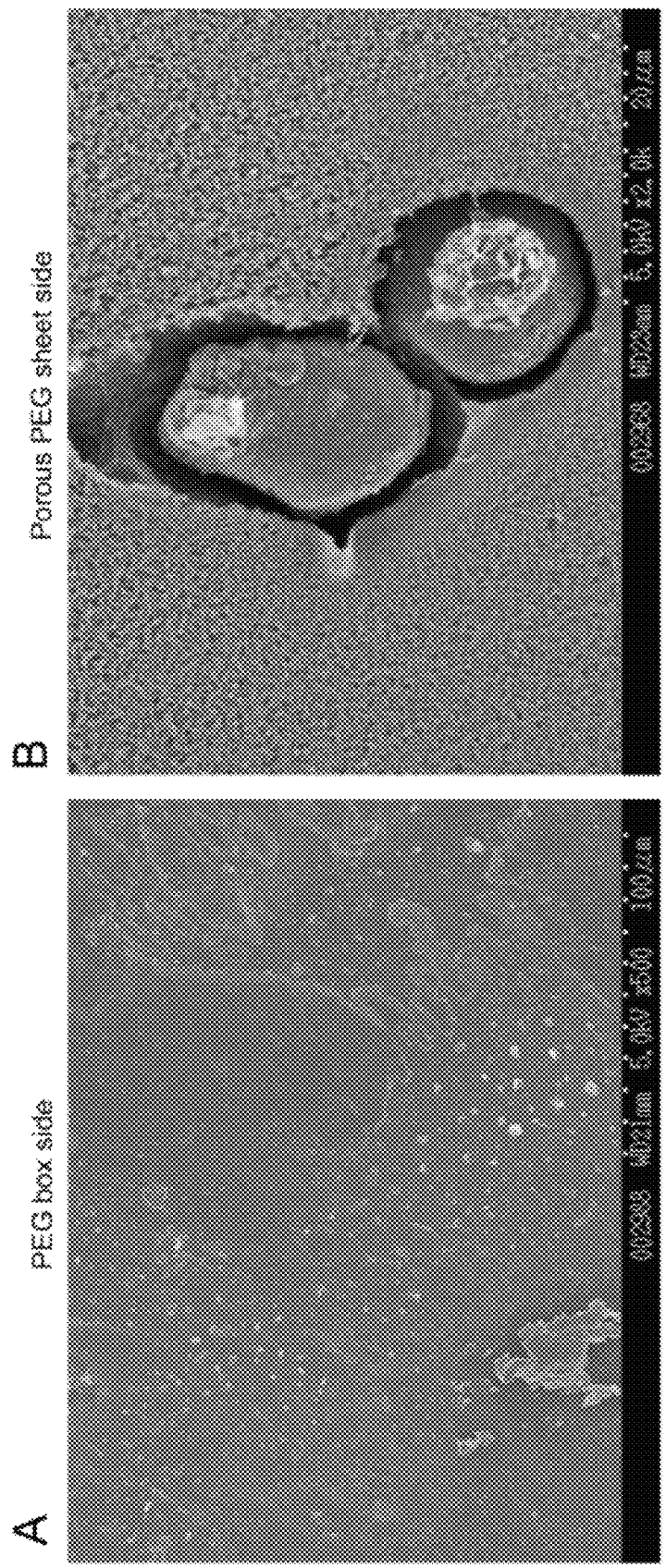
FIG. 24 is a pair of photographs showing SEM images of the surface structure of a PEG capsule having been implanted for one month.

The capsule implanted for 1 month was removed and subjected to structural evaluation using SEM. The capsule could be easily detached from the sclera. An SEM sample was prepared by paraformaldehyde fixation, osmium fixation, ethanol dehydration, critical point drying, and osmium coating, and subjected to SEM observation (5 kV). The photograph is shown in FIG. 24. The PEG box surface was little biodegraded and produced little reaction with the body, showing that the box was highly biocompatible (FIG. 24A). A capsule using a porous PEGDM sheet having collagen particles left without digestion was also employed for implantation; it is shown that the collagen particles remain without degradation (FIG. 24B) and substantially no inflammatory cells infiltrate, indicating a good biocompatibility. The present non-degradable capsule DDS can probably maintain its slow-releasing performance over a long period of time.

From the present Examples, the present invention was shown to have the following features.

(1) The porous PEG sheet porosity and the included drug-packing form of the capsule can be changed to change its slow-releasing characteristics.

(2) Linear slow release in which the initial burst is suppressed can be undergone over a long period of time.

(3) The compartmentalization of the capsule enables the charge of several drugs and the change of the form of packing them can change slow-releasing characteristics. Thus, a plurality of drugs can be slowly released simultaneously at different speeds.

(4) The scleral DDS does not cause a feeling of a foreign body because of its compact size.

(5) Because PEG, less bioactive, is used, reactions such as inflammatory reaction and fiber formation do not occur, leading to long-term function in the body.

(6) Removal/exchange is possible in the case of unnecessity.

INDUSTRIAL APPLICABILITY

The DDS of the present invention uses a box-shaped PEG containing a drug and capped with a porous PEG sheet as an implant and is implanted in an affected part. The drug is slowly released from the box-shaped PEG through the porous PEG sheet, enabling the sustained administration of the drug. In addition, Collagen impregnated a drug (as used herein, the form of collagen may be a gel or particles) or a pellet having the collage embedded in photo-curable polyethylene glycol (PEG) is placed in the box-shaped PEG to produce the slow release of the drug from the collagen to the inside of the box-shaped PEG and further cause the slow release thereof through the porous PEG sheet to the outside of the PEG box; thus, the drug is slowly released for a long period of time without the initial burst. Thus, the DDS of the present invention enables the stepwise slow release of a drug. Collagen is originally used as a base material for a slow release base material; however, according to the DDS of the present invention, the dispersion of a drug into the solvent is suppressed since PEG inhibits the contact between collagen and the solvent, enabling the prolongation of a slow release period. Collagen is held in PEG, not dispersed or leaked to the outside, and can be removed together with PEG when unnecessary. Thus, when implanted on the sclera, it can be simply removed by treatment during outpatient visit. In the DDS of the present invention, collagen is present in a state of being closed in a capsule; when the collagen is exposed to the body, the collagen can adhere to cells to cause biological reactions such as fiber formation, capsulation, and adhesion. In the DDS of the present invention, collagen is present in PEG; thus, the collagen does not contact cells and produces no biological reaction. PEG is a less bioreactive base material and does not produce biological reactions.

In addition, the DDS capable of unidirectional slow release can be patched on the side of the sclera in a treatment site to produce the slow release of a drug into the eyeball to conserve the degenerated retina and glaucoma.

The DDS of the present invention is a long-term slow release DDS effective against a disease for which the sustained administration of a drug into the body is desired, particularly a disease for which the sustained local administration thereof is desired, is particularly a system for sustainably delivering a drug for treating a disease such as eye disease to an affected part such as the inside of the eye, and enables drug administration to the affected part over a long period of time because of its slow-releasing capability.

All publications, patents, and patent applications cited in this application are intended to be incorporated herein by reference in their entirety.

The invention claimed is:

1. A drug-slow releasing implant, wherein the implant is a PEG capsule internally comprising a PEG pellet comprising collagen impregnated with a therapeutic drug, wherein the PEG capsule is capped with a porous PEG sheet and the therapeutic drug is released through the porous PEG sheet.

2. The drug slow-releasing implant according to claim 1, wherein the implant is a stepwise slow-releasing implant in which the collagen impregnated with the therapeutic drug or the PEG pellet comprising collagen impregnated with the therapeutic drug is internally comprised in the PEG capsule.

3. The drug slow-releasing implant according to claim 1, wherein the therapeutic drug for impregnation is in the form of a solution, powdered particles, or a mixture thereof.

4. The drug slow-releasing implant according to claim 1, wherein the PEG pellet comprising collagen impregnated with the therapeutic drug is prepared by mixing the collagen impregnated with the therapeutic drug, a photo-curable polyethylene glycol, and a photopolymerization initiator and curing the mixture with UV light.

5. The drug slow-releasing implant according to claim 1, wherein the PEG capsule is prepared by mixing a photo-curable polyethylene glycol and a photopolymerization initiator and curing the mixture with UV light.

6. The drug slow-releasing implant according to claim 1, wherein the porous PEG sheet is prepared by mixing a photo-curable polyethylene glycol solution, collagen particles, and a photopolymerization initiator, irradiating the mixture with UV light for curing, and when digesting the collagen particles.

7. The drug slow-releasing implant according to claim 4, wherein the photo-curable polyethylene glycol is selected from the group consisting of polyethylene glycol dimethacrylate (PEGDM), polyethylene glycol methacrylate (PEGMA), and polyethylene glycol diacrylate (PEGDA).

8. The drug slow-releasing implant according to claim 1, wherein the implant is for treating eye disease and implanted in the sclera that is a portion from above the choroid to under the conjunctiva, that is, the subsclera, the inside of the sclera, the episclera, the subconjunctiva, and the suprachoroid.

9. The drug slow-releasing implant according to claim 8, wherein the eye disease is a disease in which multiple factors including a gene and an environmental factor are involved, a retinal blood vessel lesion, or a disease in which inflammation or damage spreads to the choroid/retina/vitreous body.

10. The drug slow-releasing implant according to claim 9, wherein the disease in which multiple factors including a gene and an environmental factor are involved is selected from the group consisting of retinal pigmentary degeneration, age-related macular degeneration, and glaucoma; the retinal blood vessel lesion is selected from the group consisting of retinal artery occlusion, branch retinal vein occlusion, and diabetic retinopathy; and the disease in which inflammation or damage spreads to the choroid/retina/vitreous body is uveitis.

11. The drug slow-releasing implant according to claim 1, wherein the therapeutic drug is selected from the group consisting of a drug suppressing vascularization, a drug promoting the growth of nerve cells, a steroid drug, a therapeutic drug for glaucoma, an anti-inflammatory drug, an antifungal drug, and an anticancer drug.

12. A sustained drug delivery system in which an implant is implanted in the body, wherein the implant is the drug slow-releasing implant according to claim 1.

* * * * *